(12) United States Patent
Weaver et al.

(10) Patent No.: US 11,129,403 B2
(45) Date of Patent: Sep. 28, 2021

(54) USES OF SOLUBLE CORN FIBER FOR INCREASING COLONIC BACTERIA POPULATIONS AND INCREASING MINERAL ABSORPTION

(71) Applicants: Tate & Lyle Ingredients Americas LLC, Hoffman Estates, IL (US); Purdue Research Foundation, West Lafayette, IN (US)

(72) Inventors: Connie Marie Weaver, West Lafayette, IN (US); Cindy H. Nakatsu, West Lafayette, IN (US); Patricia Williamson, West Dundee, IL (US); Andrew Joseph Hoffman, West Point, IN (US); Lisa Marie Sanders, Battle Creek, MI (US)

(73) Assignee: Tate & Lyle Ingredients Americas LLC, Hoffman Estates, IL (US)

(*) Notice: Subject to any disclaimer, the term of this patent is extended or adjusted under 35 U.S.C. 154(b) by 0 days.

(21) Appl. No.: 14/778,883

(22) PCT Filed: Mar. 22, 2014

(86) PCT No.: PCT/US2014/031526
§ 371 (c)(1),
(2) Date: Sep. 21, 2015

(87) PCT Pub. No.: WO2014/153554
PCT Pub. Date: Sep. 25, 2014

(65) Prior Publication Data
US 2016/0058056 A1    Mar. 3, 2016

Related U.S. Application Data

(60) Provisional application No. 61/804,584, filed on Mar. 22, 2013.

(51) Int. Cl.
| A23L 29/212 | (2016.01) |
| A23L 33/00 | (2016.01) |
| A23L 33/22 | (2016.01) |
| A23L 33/21 | (2016.01) |

(52) U.S. Cl.
CPC .............. *A23L 33/30* (2016.08); *A23L 33/21* (2016.08); *A23L 33/22* (2016.08); *A23V 2002/00* (2013.01)

(58) Field of Classification Search
CPC ........ A23L 1/3081; A23L 1/293; A23L 33/30; A23L 33/21; A23L 33/22
USPC .......................................................... 426/2
See application file for complete search history.

(56) References Cited

U.S. PATENT DOCUMENTS

| 4,110,477 A | 8/1978 | Naruse et al. |
| 6,203,797 B1 | 3/2001 | Perry |
| 6,811,786 B1 | 11/2004 | Farmer et al. |
| 6,849,256 B1 | 2/2005 | Farmer |
| 6,905,692 B2 | 6/2005 | Farmer |
| 6,942,754 B2 | 9/2005 | Izumi et al. |
| 7,608,436 B2 | 10/2009 | Harrison et al. |
| 8,057,840 B2 | 11/2011 | Harrison et al. |
| 2003/0077255 A1 | 4/2003 | Sabharwal |
| 2004/0219157 A1 | 11/2004 | Rochat |
| 2004/0253690 A1 | 12/2004 | Kubota |
| 2005/0079244 A1 | 4/2005 | Giffard et al. |
| 2005/0095350 A1 | 5/2005 | Barresi |
| 2005/0271643 A1 | 12/2005 | Sorokulova et al. |
| 2006/0210696 A1 | 9/2006 | Liu et al. |
| 2007/0172931 A1* | 7/2007 | Harrison ................. C12P 19/04 435/101 |
| 2008/0102162 A1 | 5/2008 | Delcour et al. |
| 2008/0175977 A1* | 7/2008 | Harrison ................. A23L 21/00 426/659 |
| 2008/0199444 A1 | 8/2008 | Cui et al. |
| 2008/0254166 A1* | 10/2008 | Potter ..................... A23L 33/26 426/61 |
| 2008/0292766 A1* | 11/2008 | Hoffman ................. A21D 2/18 426/548 |
| 2012/0027734 A1* | 2/2012 | Van Immerseel .... A61K 35/741 424/93.44 |
| 2015/0209383 A1* | 7/2015 | Boileau ................. A61K 31/765 514/58 |

FOREIGN PATENT DOCUMENTS

| CA | 2007270 | 8/1990 |
| CN | 101537020 | 9/2009 |
| CN | 101744239 | 6/2010 |
| EP | 1243273 | 9/2002 |
| JP | S61-219392 A | 9/1986 |
| JP | S63-109791 A | 5/1988 |
| JP | H03-175989 A | 7/1991 |
| WO | 2004/052121 | 6/2004 |
| WO | 2007/050656 | 5/2007 |

(Continued)

OTHER PUBLICATIONS

Maathuis, A. et al. J. Am. College Nut. 28 (2008), 657-666 (Abstract).*
Hooda, S. et al. J. Nutr. 142: 1259-1265 (2012).*
Saarinnen, M. T. et al. 2012. Biosci. Biotechnol. Biochem. 76: 1135-1139 (Year: 2012).*
Lopez, H. W. et al. 1999. J. Nutr. Biochem. 10: 500-509 (Year: 1999).*
Walker, A. W. et al. IMSE J. 5: 220-230 (2011) (Year: 2011).*
Martinez, I. et al. Plos ONE. 5: 1-11 (2010) (Year: 2010).*
Bassaganaya-Riera et al., "Soluble fibers and resistant starch ameliorate disease activity in interleukin-10-deficient mice with inflammatory bowel disease," J. Nutr. 141(7):1318-25 (May 2011).

(Continued)

*Primary Examiner* — Hamid R Badr
(74) *Attorney, Agent, or Firm* — McDonnell Boehnen Hulbert & Berghoff LLP

(57) ABSTRACT

The present invention relates to fermentable soluble fibers, such as soluble corn fiber (SCF), and its uses in increasing colonic bacteria populations, and edible compositions useful in increasing colonic bacteria populations.

24 Claims, 9 Drawing Sheets

(56) References Cited

FOREIGN PATENT DOCUMENTS

| WO | 2009/026306 | 2/2009 |
|---|---|---|
| WO | 2009/051977 | 4/2009 |
| WO | 2010/015580 | 2/2010 |
| WO | 2012/027214 | 3/2012 |
| WO | 2012089782 A1 | 7/2012 |
| WO | 2013/067146 | 5/2013 |
| WO | 2014/153554 | 9/2014 |

OTHER PUBLICATIONS

Boler et al., "Digestive physiological outcomes related to polydextrose and soluble maize fibre consumption by healthy adult men," Br. J. Nutr. 106:1864-71 (May 2011).
Bosscher, "Chapter 6:Fructan Prebiotics Derived from Inulin," Prebiotics and Probiotics Science and Technology, vol. 1, 169-70 (Jun. 2009).
Canani et al., "Probiotics for treatment of acute diarrhoea in children: randomised clinical trial of five different preparations," BMJ 335(7615):340 (Aug. 2007).
Casula et al., "Bacillus Probiotics: Spore Germination in the Gastrointestinal Tract," Appl. Environ. Microbiol. 68(5):2344-52 (May 2002).
De Vecchi et al., "Lactobacillus Sporogenes or Bacillus Coagulans: Misidentification or Mislabelling?" International Journal of Probiotics and Prebiotics 1(1):3-10 (2006).
"Dose Effects of SCF on Calcium Metabolism and GI Microflora in Adolescents," https://clinicaltrials.gov/ct2/show/study/NCT01660503, Purdue University, pp. 1-3 (Aug. 2012).
Duc et al., "Characterization of Bacillus probiotics available for human use," Appl. Environ. Microbiol.70(4):2161-71 (Apr. 2004).
Englyst et al., "Classification and measurement of nutritionally important starch fractions," Eur. J. Clin. Nutr. 46(2):S33-50 (Oct. 1992).
FAO Technical Meeting on Prebiotics, Food Quality and Standards Service, Food and Agriculture Organization of the United Nations (Sep. 2007).
FoodMinds, "New research: Soluble corn fiber plays important role in gut health and calcium absorption," http://www.eurekalert.org/pub_releases/2012-09/fl-rs090512.php, pp. 1-3 (Sep. 2012).
Fujiya et al., "The Bacillus subtilis quorum-sensing molecule CSF contributes to intestinal homeostasis via OCTN2, a host cell membrane transporter," Cell Host Microbe 1(4):299-308 (Jun. 2007).
Giannini et al., "Role of partially hydrolyzed guar gum in the treatment of irritable bowel syndrome," Nutrition 22 (3):334-42 (Jan. 2006).
Gibson, "Dietary modulation of the human gut microflora using prebiotics," Br. J. Nutr. 80(4):S209-12 (Oct. 1998).
Gibson, "Dietary modulation of the human gut microflora using the prebiotics oligofructose and inulin," J. Nutr. 129(7 Suppl):1438S-41S (Jul. 1999).
Green et al., "Characterization of two Bacillus probiotics," Appl. Environ. Microbiol. 65(9):4288-91 (Sep. 1999).
Guo et al., "Screening of Bacillus strains as potential probiotics and subsequent confirmation of the in vivo effectiveness of Bacillus subtilis MA139 in pigs," Antonie Van Leeuwenhoek 90(2):139-46 (Jul. 2006).
Hartemink, R., "Bacillus coagulans (Lactobacillus sporogenes) a probiotic?" Food-Info, www.food-info.net/uklff/sporogenes.htm (2007).
Hooda et al., "454 pyrosequencing reveals a shift in fecal microbiota of healthy adult men consuming polydextrose or soluble corn fiber," J. Nutr. 142(7):1259-65 (May 2012).
Jahoor et al., "Peroxisome proliferator-activated receptors mediate host cell proinflammatory responses to Pseudomonas aeruginosa autoinducer," J. Bacteriol. 190(13):4408-15 (Jan. 2008).
La Rosa et al., "Prevention of antibiotic-associated diarrhea with Lactobacillus sporogens and fructo-oligosaccharides in children. A multicentric double-blind vs placebo study," Minerva Pediatr. 55(5):447-52 (Oct. 2003), Spanish language publication with English language abstract.
Leser et al., "Germination and outgrowth of Bacillus subtilis and Bacillus licheniformis spores in the gastrointestinal tract of pigs," J. Appl. Microbiol. 104(4):1025-33 (Nov. 2007).
Maathuis et al., "The effect of the undigested fraction of maize products on the activity and composition of the microbiota determined in a dynamic in vitro model of the human proximal large intestine," J. Am. Coll. Nutr. 28(6):657-66 (Dec. 2009).
Marseglia et al., "Efficacy of Bacillus clausii spores in the prevention of recurrent respiratory infections in children: a pilot study," Ther. Clin. Risk Manag. 3(1):13-7 (Mar. 2007).
Mazza, "The use of Bacillus subtilis as an antidiarrhoeal microorganism," Boll. Chim. Farm. 133(1):3-18 (Jan. 1994).
NewHope360, "Tate & Lyle launches second PROMITOR(TM) dietary fiber," http://newhope.com/managing-your-business/tate-lyle-launches-second-promitortm-dietary-fiber, pp. 1-3 (Jul. 2007).
Nyman et al., "Dietary Fiber Content and Composition in Six Cereals at Different Extraction Rates," Cereal Chemistry 61(1):14-9 (1984).
Palframan et al., "Development of a quantitative tool for the comparison of the prebiotic effect of dietary oligosaccharides," Lett. Appl. Microbiol. 37(4), 281-4 (Aug. 2003).
Roberfroid et al., "The bifidogenic nature of chicory inulin and its hydrolysis products," J. Nutr. 128(1):11-9 (Jan. 1998).
Shibanuma et al., "Partial Acid Hydrolysis of Corn Fiber for the Production of L-Arabinose," Journal of Applied Glycoscience 46(3):249-56 (1999).
Slavin et al., "Partially hydrolyzed guar gum: clinical nutrition uses," Nutrition 19(6):549-52 (Jun. 2003).
"Soluble Corn Fibre*: Health Benefits and Product Applications," http://www.foodnutritionknowledge.info/Documents/TL%20Soluble%20Corn%20Fibre%20Brochure2013.pdf, pp. 1-8 (2013).
Spinosa et al., "On the fate of ingested Bacillus spores," Res. Microbiol. 151(5):361-8 (Jun. 2000).
Sugawa-Katayama et al., "Effects of Pullulan, Polydextrose and Pectin on Cecal Microflora," Oyo Toshitsu Kagaku 41(4):413-8 (1994).
Tuohy et al. "A Human Volunteer Study to Determine the Prebiotic Effects of Lactulose Powder on Human Colonic Microbiota," Microbial Ecology in Health and Disease 14(3):165-173 (2002).
Urdaci et al., "Bacillus clausii probiotic strains: antimicrobial and immunomodulatory activities," J. Clin. Gastroenterol. 38(6 Suppl):S86-90 (Jul. 2004).
Weaver et al., "Novel fibers increase bone calcium content and strength beyond efficiency of large intestine fermentation," J. Agric. Food Chem. 58(16):8952-7 (Aug. 2010).
Whisner et al., "Soluble corn fiber effects on calcium absorption and retention in adolescent girls and boys," FASEB J. 26(1):373.4 (Apr. 2012).
Whisner et al., "Galacto-oligosaccharides increase calcium absorption and gut bifidobacteria in young girls: a double-blind cross-over trial," Br. J. Nutr. 110(7):1292-303 (Mar. 2013).
Whisner et al., "Soluble maize fibre affects short-term calcium absorption in adolescent boys and girls: a randomised controlled trial using dual stable isotopic tracers," Br. J. Nutr. 112(3):446-56 (May 2014).
Yajun, "Study on Proliferation Effect of Water-Soluble Dietary Fibers on Intestinal Probiotics," Food Sci. and Tech. (China) 10:130-3, with English translation.
EurekAlert, "New research: Soluble corn fiber plays important role in gut health and calcium absorption," Sep. 6, 2012, available at http://www.eurekalert.org/pub_releases/2012-09/fl-rs090512.php.
C.M. Whisner et al., "Soluble corn fiber modulates calcium absorption by altering colonic microbiota," FASEB Journal, published online Apr. 1, 2013 (Abstract only).
A. P. Clavijo-Gutierrez, "Response of Human Gut Microbiota to Diet Supplementation with Soy or Soluble Corn Fiber," Dissertation, Purdue University, May 2013.
International Preliminary Report on Patentability, International Patent Application No. PCT/US2014/031526, dated Sep. 22, 2015.

* cited by examiner

USES OF SOLUBLE CORN FIBER FOR INCREASING COLONIC BACTERIA POPULATIONS AND INCREASING MINERAL ABSORPTION

CROSS-REFERENCE TO RELATED APPLICATIONS

This application claims the benefit of priority of U.S. Provisional Patent Application Ser. No. 61/804,584, filed Mar. 22, 2013, which is hereby incorporated herein by reference in its entirety.

BACKGROUND OF THE INVENTION

1. Field of the Invention

The present invention relates generally to fermentable soluble fibers, such as soluble corn fiber (SCF), and uses and compositions thereof. In certain aspects, the present invention relates to methods of increasing colonic bacteria populations in a subject.

2. Summary of the Related Art

The gut microflorae form a complex ecosystem that interacts with host cells and nutrients. An adult human body contains a living bacterial biomass of greater than $10^{14}$ and more than 400 different species, which represents the largest, densest, and most diverse microbial community in the human body. The presence of the gut bacteria is a part of normal human physiology and is important for the development of gut functions, harvesting energy from dietary carbohydrates, harvesting essential vitamins and metabolizing environmental chemicals in the gut. Recent studies further suggested that gut bacteria may be involved in fat storage and affect weight gain and loss. Gut bacteria is also involved in maturation of the immune system, is in constant communication with the immune system, and protection against pathogens. Given the importance of gut bacteria in health and wellness, a strong interest in functional food ingredients to enhance the populations of beneficial gut bacteria has emerged.

Adolescence is an important life-stage for bone health providing a unique opportunity to maximize mineral retention and prevent the risk of osteoporosis-related fractures later in life. Because calcium is becoming increasingly deficient in the diet due to decreasing milk consumption, a strong interest in functional food ingredients to enhance calcium utilization has emerged.

SUMMARY OF THE INVENTION

In one broad aspect, the invention provides a method of increasing one or more colonic bacteria populations in a subject, the method comprising orally administering to the subject a composition comprising a fermentable soluble fiber. In another aspect, the invention provides a method of increasing one or more colonic bacteria populations in a subject, the method comprising orally administering to the subject a composition comprising soluble corn fiber.

In one aspect the invention provides a method of increasing one or more colonic bacteria populations selected from the genera *Parabacteroides, Butyricicoccus, Oscillibacter,* and *Dialister* in a subject, the method comprising orally administering to the subject a composition comprising a fermentable soluble fiber. In another aspect the invention provides a method of increasing one or more colonic bacteria populations selected from *Parabacteroides, Butyricicoccus, Oscillibacter,* and *Dialister* in a subject, the method comprising orally administering to the subject a composition comprising soluble corn fiber.

In another aspect the invention provides a method of increasing one or more colonic bacteria populations selected from the genera *Bacteroides, Butyricicoccus, Oscillibacter,* and *Dialister* in a subject, the method comprising orally administering to the subject a composition comprising a fermentable soluble fiber (e.g., soluble corn fiber).

In another aspect the invention provides a method of increasing one or more colonic bacteria populations selected from the genera *Parabacteroides, Bifidobacterium, Alistipes, Anaerococcus, Catenibacterium,* genera within the order Clostridiales, and genera within the family Ruminococcaceae in a subject, the method comprising orally administering to the subject a composition comprising a fermentable soluble fiber (e.g., soluble corn fiber).

In another aspect the invention provides a method of increasing one or more colonic bacteria populations selected from the genera *Parabacteroides, Dialister, Akkermansia,* and genera within the family Lachnospiraceae in a subject, the method comprising orally administering to the subject a composition comprising a fermentable soluble fiber (e.g., soluble corn fiber).

In another aspect, the invention provides a method of increasing one or more colonic bacteria populations in a subject, the method comprising orally administering to the subject a composition comprising a fermentable soluble fiber, such as soluble corn fiber, at least about 3 g/day, at least about 5 g/day, at least about 10 g/day, at least about 15 g/day, at least about 20 g/day or even at least about 25 g/day.

In another aspect, the invention provides a method of increasing one or more colonic bacteria populations in a subject, the method comprising orally administering to the subject a composition comprising a fermentable soluble fiber, such as soluble corn fiber such that there is a decrease in fecal pH to a value below about 5.5 (e.g., a decrease in fecal pH from about 7 to about 4.5). Such decrease, can for example, result in an increase in the bioavailability of calcium.

In another aspect, the invention provides a method of decreasing fecal pH to a value no more than about 5.5 (e.g., to a fecal pH of about 4.5), the method comprising orally administering to the subject a composition comprising a fermentable soluble fiber, such as soluble corn fiber.

In another aspect, the invention provides a method of increasing mineral (e.g., calcium, iron, zinc, copper, potassium and/or magnesium) absorption in a subject, the method comprising orally administering to the subject a composition comprising a fermentable soluble fiber, such as soluble corn fiber. In certain embodiments of the methods and compositions as described herein, the mineral is absorbed as a divalent cation. In certain embodiments of the methods and compositions as described herein, the mineral is calcium. In other embodiments of the methods and compositions as described herein, the mineral is calcium and/or magnesium. In certain embodiments of the methods and compositions as described herein, the mineral is calcium and/or iron. In other embodiments of the methods and compositions as described herein, the mineral is calcium, magnesium and/or iron.

In another aspect, the invention provides a method of increasing mineral (e.g., calcium, iron, zinc, copper, potassium/or and magnesium, as described above) absorption in a subject, the method comprising orally administering to the subject a composition comprising a fermentable soluble fiber, such as soluble corn fiber, at a rate of at least about 3 g/day, at least about 5 g/day, at least about 10 g/day, at least about 12 g/day, at least about 15 g/day, at least about 20 g/day or even at least about 25 g/day.

In another aspect, the invention provides an edible product comprising a fermentable soluble fiber, such as soluble corn fiber, and one or more bacterial populations selected from the group consisting of *Lactobacillus, Bacteroides, Parabacteroides, Alistipes, Bifidobacterium, Butyricicoccus, Oscillibacter, Dialister* and any combinations thereof.

In another aspect the invention provides an edible composition comprising one or more (e.g., two or more or three or more) bacteria populations selected from the genera (e.g., each selected from a different genus) *Bacteroides, Butyricicoccus, Oscillibacter,* and *Dialister*. The edible composition can optionally include a fermentable soluble fiber (e.g., soluble corn fiber).

In another aspect the invention provides an edible composition comprising one or more (e.g., two or more or three or more) bacteria populations selected from the genera (e.g., each selected from a different genus) *Parabacteroides, Dialister, Akkermansia,* and genera within the family Lachnospiraceae. The edible composition can optionally include a fermentable soluble fiber (e.g., soluble corn fiber).

In another aspect the invention provides an edible composition comprising one or more (e.g., two or more or three or more) bacteria populations selected from the genera (e.g., each selected from a different genus) *Parabacteroides, Bifidobacterium, Alistipes, Anaerococcus, Catenibacterium,* genera within the order Clostridiales; and genera within the family Ruminococcaceae. The edible composition can optionally include a fermentable soluble fiber (e.g., soluble corn fiber).

BRIEF DESCRIPTION OF THE DRAWINGS

The invention set forth herein can be advantageously understood with regard to the drawings.

DETAILED DESCRIPTION

Figure 1:
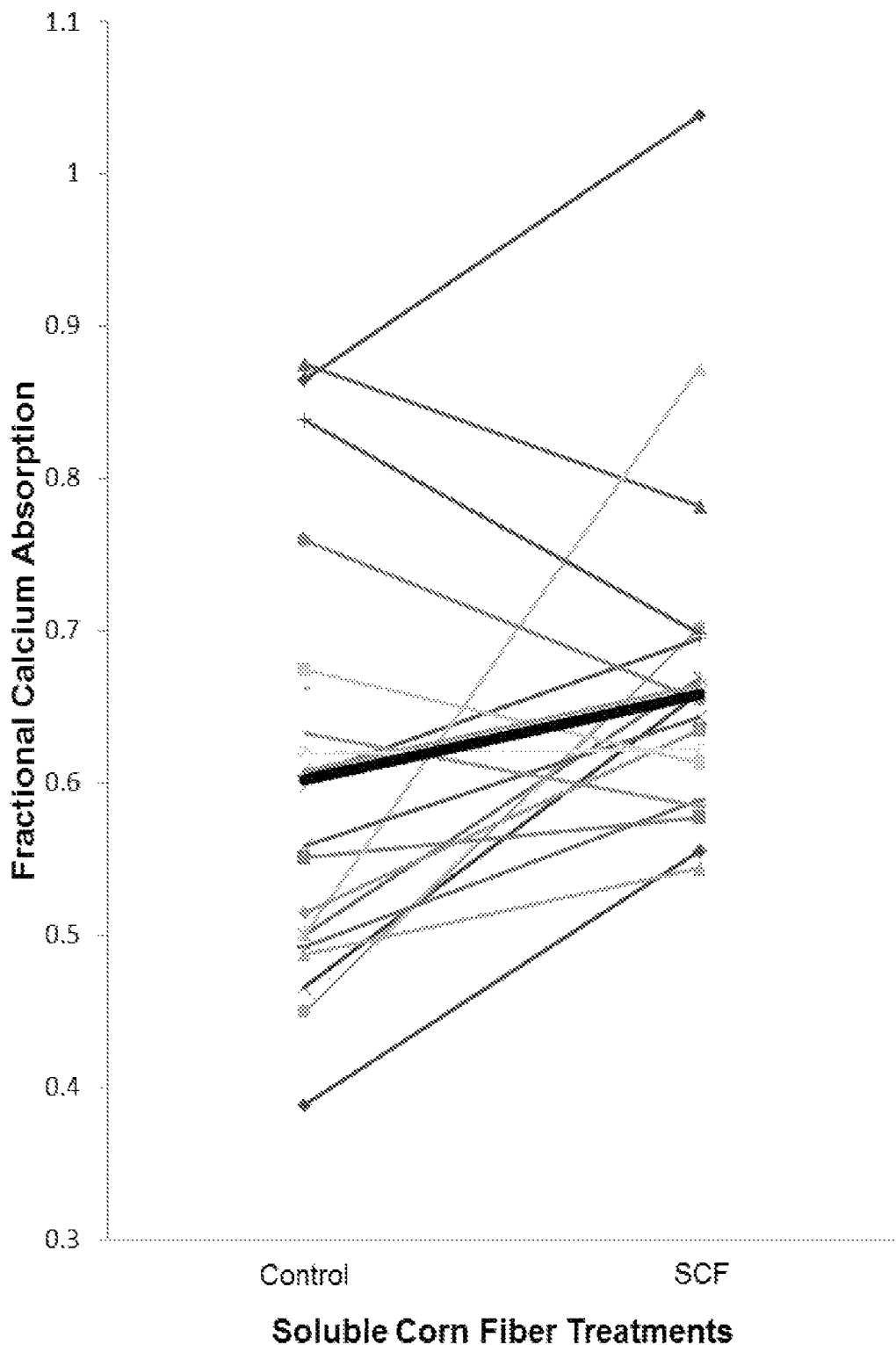
FIG. 1 shows the effect of SCF on fractional calcium absorption (mean+SEM) during Day 1 and Day 2 following a calcium absorption test with dual stable isotopes in early adolescent boys and girls. A general linear model that included treatment, sequence, and phase for each time period (0-24 h and 24-48 h) indicated that calcium absorption for SCF was higher than that for control at 24-48 h (*P=0.02) but not at 0-24 h (P=0.09).

Before the disclosed methods and materials are described, it is to be understood that the aspects described herein are not limited to specific embodiments, methods, or compositions, and as such can, of course, vary. It is also to be understood that the terminology used herein is for the purpose of describing particular aspects only and, unless specifically defined herein, is not intended to be limiting.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

In view of the present disclosure, the methods and compositions described herein can be configured by the person of ordinary skill in the art to meet the desired need. In general, the disclosed methods and compositions provide improvements in gut microbiota. For example, in certain aspects, the methods of the disclosure increase one or more colonic bacteria populations that are capable of fermentation and short chain fatty acid production.

For example, in certain embodiments of the methods and compositions described herein, administering a composition comprising a fermentable soluble fiber, such as soluble corn fiber increases the population of one or more colonic bacteria populations, each from a genus selected from the group consisting of *Parabacteroides, Butyricicoccus, Oscillibacter,* and *Dialister*, and any combination thereof. For example, in one embodiment of the methods and compositions described herein, administering a composition comprising a fermentable soluble fiber, e.g., soluble corn fiber, increases the population of *Parabacteroides*. In another embodiment of the methods and compositions described herein, administering a composition comprising a fermentable soluble fiber, e.g., soluble corn fiber, increases the population of *Butyricicoccus*. In another embodiment of the methods and compositions described herein, administering a composition comprising a fermentable soluble fiber, e.g., soluble corn fiber, increases the population of *Oscillibacter*. In another embodiment of the methods and compositions described herein, administering a composition comprising a fermentable soluble fiber, e.g., soluble corn fiber, increases the population of *Dialister*. For example, in certain embodiments of the methods and compositions described herein, administering a composition comprising a fermentable soluble fiber, e.g., soluble corn fiber, increases the population of *Parabacteroides* and *Butyricicoccus*; *Parabacteroides* and *Oscillibacter*; *Parabacteroides* and *Dialister*; *Butyricicoccus* and *Oscillibacter*; *Butyricicoccus* and *Dialister*; *Oscillibacter* and *Dialister*; *Parabacteroides*, *Butyricicoccus* and *Oscillibacter*; *Parabacteroides*, *Butyricicoccus* and *Dialister*; *Parabacteroides*, *Oscillibacter*, and *Dialister*; *Butyricicoccus*, *Oscillibacter*, and *Dialister*; or *Parabacteroides*, *Butyricicoccus*, *Oscillibacter*, and *Dialister*. Of course, other bacterial populations can additionally be increased. In certain such embodiments, absorption of calcium also increases (e.g., as described below).

For example, in certain embodiments of the methods and compositions described herein, administering a composition comprising a fermentable soluble fiber, such as soluble corn fiber increases the population of one or more colonic bacteria populations, each from a genus selected from the group consisting of *Bacteroides, Butyricicoccus, Oscillibacter*, and *Dialister*, and any combination thereof. For example, in one embodiment of the methods and compositions described herein, administering a composition comprising a fermentable soluble fiber, e.g., soluble corn fiber, increases the population of *Bacteroides*. In another embodiment of the methods and compositions described herein, administering a composition comprising a fermentable soluble fiber, e.g., soluble corn fiber, increases the population of *Butyricicoccus*. In another embodiment of the methods and compositions described herein, administering a composition comprising a fermentable soluble fiber, e.g., soluble corn fiber, increases the population of *Oscillibacter*. In another embodiment of the methods and compositions described herein, administering a composition comprising a fermentable soluble fiber, e.g., soluble corn fiber, increases the population of *Dialister*. For example, in certain embodiments of the methods and compositions described herein, administering a composition comprising a fermentable soluble fiber, e.g., soluble corn fiber, increases the population of *Bacteroides* and *Butyricicoccus*; *Bacteroides* and *Oscillibacter*; *Bacteroides* and *Dialister*; *Butyricicoccus* and *Oscillibacter*; *Butyricicoccus* and *Dialister*; *Oscillibacter* and *Dialister*; *Bacteroides, Butyricicoccus* and *Oscillibacter*; *Bacteroides, Butyricicoccus* and *Dialister*; *Bacteroides, Oscillibacter*, and *Dialister*; *Butyricicoccus, Oscillibacter*, and *Dialister*; or *Bacteroides, Butyricicoccus, Oscillibacter*, and *Dialister*. Of course, other bacterial populations can additionally be increased. In certain such embodiments, absorption of calcium also increases (e.g., as described below).

In other embodiments of the methods and compositions described herein, administering a composition comprising a fermentable soluble fiber, such as soluble corn fiber increases the population of one or more colonic bacteria populations, each from a genus selected from the group consisting of *Parabacteroides, Bifidobacterium, Alistipes, Anaerococcus, Catenibacterium*, genera within the order Clostridiales (e.g., not *Clostridium, Anaerofustis, Anaerococcus, Coprococcus, Peptostreptococcaceae, Sporacetigenium*); and genera within the family Ruminococcaceae and any combination thereof. For example, in one embodiment of the methods and compositions described herein, administering a composition comprising a fermentable soluble fiber, e.g., soluble corn fiber, increases the population of *Parabacteroides*. In another embodiment of the methods and compositions described herein, administering a composition comprising a fermentable soluble fiber, such as soluble corn fiber increases the population of *Bifidobacterium*. In another embodiment of the methods and compositions described herein, administering a composition comprising a fermentable soluble fiber, such as soluble corn fiber increases the population of *Alistipes*. In another embodiment of the methods and compositions described herein, administering a composition comprising a fermentable soluble fiber, such as soluble corn fiber increases the population of *Anaerococcus*. In another embodiment of the methods and compositions described herein, administering a composition comprising a fermentable soluble fiber, such as soluble corn fiber increases the population of *Catenibacterium*. In another embodiment of the methods and compositions described herein, administering a composition comprising a fermentable soluble fiber, such as soluble corn fiber increases the population of the family Ruminococcaceae. In another embodiment of the methods and compositions described herein, administering a composition comprising a fermentable soluble fiber, such as soluble corn fiber increases the population of the order Clostridiales. For example, in certain embodiments of the methods and compositions described herein, administering a composition comprising a fermentable soluble fiber, e.g., soluble corn fiber, increases the population of *Parabacteroides* and *Bifidobacterium*; *Parabacteroides* and *Alistipes*; *Parabacteroides* and *Anaerococcus*; *Parabacteroides* and *Catenibacterium*; *Parabacteroides* and Ruminococcaceae; *Parabacteroides* and Clostridiales; *Bifidobacterium* and *Alistipes*; *Bifidobacterium* and *Anaerococcus*; *Bifidobacterium* and *Catenibacterium*; *Bifidobacterium* and Ruminococcaceae; *Bifidobacterium* and Clostridiales; *Alistipes* and *Anaerococcus*; *Alistipes* and *Catenibacterium*; *Alistipes* and Ruminococcaceae; *Anaerococcus* and *Catenibacterium*; *Anaerococcus* and Ruminococcaceae; *Anaerococcus* and Clostridiales; *Catenibacterium* and Ruminococcaceae; *Catenibacterium* and Clostridiales; Ruminococcaceae and Clostridiales; *Parabacteroides, Bifidobacterium* and *Alistipes*; *Parabacteroides, Bifidobacterium* and *Anaerococcus*; *Parabacteroides, Bifidobacterium* and *Catenibacterium*; *Parabacteroides, Bifidobacterium* and Clostridiales; *Parabacteroides, Bifidobacterium* and Ruminococcaceae; *Parabacteroides, Alistipes* and *Anaerococcus*; *Parabacteroides, Alistipes* and *Catenibacterium*; *Parabacteroides, Alistipes* and Clostridiales; *Parabacteroides, Alistipes* and Ruminococcaceae; *Parabacteroides, Anaerococcus* and *Catenibacterium*; *Parabacteroides, Anaerococcus* and Clostridiales; *Parabacteroides, Anaerococcus* and Ruminococcaceae; *Parabacteroides, Catenibacterium* and *Clostridiales; Parabacteroides, Catenibacterium* and Ruminococcaceae; *Parabacteroides*, Clostridiales and Ruminococcaceae; *Bifidobacterium, Alistipes* and *Anaerococcus*; *Bifidobacterium, Alistipes* and *Catenibacterium*; *Bifidobacterium, Alistipes* and Clostridiales; *Bifidobacterium, Alistipes* and Ruminococcaceae; *Bifidobacterium, Anaerococcus* and *Catenibacterium*; *Bifidobacterium, Anaerococcus* and Clostridiales; *Bifidobacterium, Anaerococcus* and Ruminococcaceae; *Bifidobacterium, Catenibacterium* and Clostridiales; *Bifidobacterium, Catenibacterium* and Ruminococcaceae; *Bifidobacterium*, Clostridiales and Ruminococcaceae; *Alistipes, Anaerococcus* and *Catenibacterium*; *Alistipes, Anaerococcus* and Clostridiales; *Alistipes, Anaerococcus* and Ruminococcaceae; *Alistipes, Catenibacterium* and Clostridiales; *Alistipes, Catenibacterium* and Ruminococcaceae; *Alistipes,* Clostridiales and Ruminococcaceae; *Anaerococcus, Catenibacterium* and Clostridiales; *Anaerococcus, Catenibacterium* and Ruminococcaceae; *Anaerococcus,* Clostridiales and Ruminococcaceae; *Catenibacterium,* Clostridiales and Ruminococcaceae; *Parabacteroides, Bifidobacterium, Alistipes* and *Anaerococcus; Parabacteroides, Bifidobacterium, Alistipes* and *Catenibacterium; Parabacteroides, Bifidobacterium, Alistipes* and Clostridiales; *Parabacteroides, Bifidobacterium, Alistipes* and Ruminococcaceae; *Parabacteroides, Bifidobacterium, Anaerococcus* and *Catenibacterium; Parabacteroides, Bifidobacterium, Anaerococcus* and Clostridiales; *Parabacteroides, Bifidobacterium, Anaerococcus* and Ruminococcaceae; *Parabacteroides, Bifidobacterium, Catenibacterium* and Clostridiales; *Parabacteroides, Bifidobacterium, Catenibacterium* and Ruminococcaceae; *Parabacteroides, Bifidobacterium,* Clostridiales and Ruminococcaceae; *Parabacteroides, Alistipes, Anaerococcus* and *Catenibacterium; Parabacteroides, Alistipes, Anaerococcus* and Clostridiales; *Parabacteroides, Alistipes, Anaerococcus* and Ruminococcaceae; *Parabacteroides, Alistipes, Catenibacterium* and Clostridiales; *Parabacteroides, Alistipes, Catenibacterium* and Ruminococcaceae; *Parabacteroides, Alistipes,* Clostridiales and Ruminococcaceae; *Parabacteroides, Anaerococcus, Catenibacterium* and *Clostridiales; Parabacteroides, Anaerococcus, Catenibacterium* and Ruminococcaceae; *Parabacteroides, Anaerococcus,* Clostridiales and Ruminococcaceae; *Parabacteroides, Catenibacterium,* Clostridiales and Ruminococcaceae; *Bifidobacterium, Alistipes, Anaerococcus* and *Catenibacterium; Bifidobacterium, Alistipes, Anaerococcus* and *Clostridiales; Bifidobacterium, Alistipes, Anaerococcus* and Ruminococcaceae; *Bifidobacterium, Alistipes, Catenibacterium* and Clostridiales; *Bifidobacterium, Alistipes, Catenibacterium* and Ruminococcaceae; *Bifidobacterium, Alistipes,* Clostridiales and Ruminococcaceae; *Bifidobacterium, Anaerococcus, Catenibacterium* and Clostridiales; *Bifidobacterium, Anaerococcus, Catenibacterium* and Ruminococcaceae; *Bifidobacterium, Anaerococcus,* Clostridiales and Ruminococcaceae; *Bifidobacterium, Catenibacterium,* Clostridiales and Ruminococcaceae; *Alistipes, Anaerococcus, Catenibacterium* and Clostridiales; *Alistipes, Anaerococcus, Catenibacterium* and Ruminococcaceae; *Alistipes, Anaerococcus,* Clostridiales and Ruminococcaceae; *Alistipes, Catenibacterium,* Clostridiales and Ruminococcaceae; or *Anaerococcus, Catenibacterium,* Clostridiales and Ruminococcaceae. Of course, the person of ordinary skill in the art will appreciate that any combination of 5, 6, or 7 colonic bacteria populations, each from a different genus selected from the group consisting of *Parabacteroides, Bifidobacterium, Alistipes, Anaerococcus, Catenibacterium,* genera within the order Clostridiales; and genera within the family Ruminococcaceae, may be increased by the methods described herein. Of course, other bacterial populations can additionally be increased.

In other embodiments of the methods and compositions described herein, administering a composition comprising a fermentable soluble fiber, such as soluble corn fiber increases the population of one or more colonic bacteria populations, each from a genus selected from the group consisting of *Parabacteroides, Dialister, Akkermansia,* and genera within the family Lachnospiraceae (e.g., not *Lachnospira*). For example, in one embodiment of the methods and compositions described herein, administering a composition comprising a fermentable soluble fiber, e.g., soluble corn fiber, increases the population of *Parabacteroides*. In another embodiment of the methods and compositions described herein, administering a composition comprising a fermentable soluble fiber, such as soluble corn fiber increases the population of *Dialister*. In another embodiment of the methods and compositions described herein, administering a composition comprising a fermentable soluble fiber, such as soluble corn fiber increases the population of *Akkermansia*. In another embodiment of the methods and compositions described herein, administering a composition comprising a fermentable soluble fiber, such as soluble corn fiber increases the population of Lachnospiraceae. For example, in certain embodiments of the methods and compositions described herein, administering a composition comprising a fermentable soluble fiber, e.g., soluble corn fiber, increases the population of *Parabacteroides* and *Dialister; Parabacteroides* and *Akkermansia; Parabacteroides* and Lachnospiraceae; *Dialister* and *Akkermansia; Dialister* and Lachnospiraceae; *Akkermansia* and Lachnospiraceae; *Parabacteroides, Dialister,* and *Akkermansia; Parabacteroides, Dialister,* and Lachnospiraceae; *Parabacteroides, Akkermansia,* and Lachnospiraceae; *Dialister, Akkermansia,* and Lachnospiraceae; or *Parabacteroides, Dialister, Akkermansia,* and Lachnospiraceae. Of course, other bacterial populations can additionally be increased.

In certain embodiments of the methods and compositions described herein, one or more of the colonic bacteria populations (e.g., as described above) are increased by at least about 5%, at least about 10%, at least about 20%, at least about 25%, at least about 30%, at least about 35%, at least about 40%, at least about 50%, at least about 60%, at least about 80%, or even at least about 100% as compared to a non-treated subject. In certain such embodiments, the colonic bacteria population is increased by no more than about 500%. In other such embodiments, the colonic bacteria population is increased by no more than about 400%. In other such embodiments, the colonic bacteria population is increased by no more than about 300%. In other such embodiments, the colonic bacteria population is increased by no more than about 200%. In other such embodiments, the colonic bacteria population is increased by no more than about 100%. In certain embodiments of the methods and compositions described herein, each of the one or more of the colonic bacteria populations (e.g., as described above) are increased by at least about 5%, at least about 10%, at least about 20%, at least about 50%, or even at least about 100% as compared to a non-treated subject. This means that there are instances where each of these bacteria may be affected independently of each other at different rates (e.g., one bacteria may increase by 50% in population, whereas another bacteria may only increase 25%). In certain such embodiments, each colonic bacteria population is increased by no more than about 500%. In other such embodiments, each colonic bacteria population is increased by no more than about 400%. In other such embodiments, each colonic bacteria population is increased by no more than about 300%. In other such embodiments, each colonic bacteria population is increased by no more than about 200%. In other such embodiments, each colonic bacteria population is increased by no more than about 100%.

In certain embodiments of the methods and compositions described herein, the proportion of one or more of the colonic bacteria populations (e.g., as described above) as a percentage of total colonic bacteria is increased by at least about 20%, at least about 25%, at least about 50%, at least about 100%, at least about 200% or even at least about 300% as compared to a non-treated subject. In certain such embodiments, the proportion of one or more of the colonic bacteria populations as a percentage of total colonic bacteria is increased by no more than about 700%. In other such embodiments, the proportion of one or more of the colonic bacteria populations as a percentage of total colonic bacteria is increased by no more than about 600%. In other such embodiments, the proportion of one or more of the colonic bacteria populations as a percentage of total colonic bacteria is increased by no more than about 500%. In other such embodiments, the proportion of one or more of the colonic bacteria populations as a percentage of total colonic bacteria is increased by no more than about 400%. In certain embodiments of the methods and compositions described herein, the proportion (i.e., as a percentage of total colonic bacteria) of each of the one or more of the colonic bacteria populations (e.g., as described above) is increased by at least about 20%, at least about 25%, at least about 50%, at least about 100%, at least about 200% or even at least about 300% as compared to a non-treated subject. This means that there are instances where each of these bacteria may be affected independently of each other at different rates (e.g., one bacteria population may increase by 50% in proportion, whereas another bacteria population may only increase 25%). In certain such embodiments, each proportion is increased by no more than about 500%. In other such embodiments, each proportion is increased by no more than about 400%. In other such embodiments, each proportion is increased by no more than about 300%. In other such embodiments, each proportion is increased by no more than about 200%. In other such embodiments, each proportion is increased by no more than about 100%.

In another embodiment, a method of increasing one or more colonic bacteria populations in a subject includes orally administering to the subject a fermentable soluble fiber, such as soluble corn fiber. In certain such embodiments, the oral administration is performed such that there is a decrease in fecal pH (e.g., as described below, to a value no more than about 5.5, for example, from a pH value of about 7 to a pH value of about 4.5). Such decrease, can for example, result in an increase in the bioavailability of minerals (e.g., divalent minerals such as calcium, as described above).

In another embodiment, the methods of the disclosure also decrease fecal pH in a subject by orally administering to the subject a fermentable soluble fiber, such as soluble corn fiber. For example, in certain embodiments of the methods and compositions as described herein, fecal pH is reduced by at least about 1.5 pH units, at least about 2 pH units, or even by at least about 2.5 pH units as compared to a non-treated subject. In certain embodiments of the methods and compositions as described herein, fecal pH is reduced to no more than about 5.5, no more than about 5, or even no more than about 4.5. In certain embodiments of the methods and compositions as described herein, fecal pH is reduced to a value in the range of about 4 to about 5.5, about 4.5 to about 5.5, about 4 to about 5, or about 4.5 to about 5. In certain embodiments, fecal pH is reduced to about 4.5, for example, from about 7 to about 4.5.

In certain embodiments of the methods and compositions as described here, the fermentable soluble fiber is soluble corn fiber. Soluble corn fiber is a starch-derived soluble fiber that is made from corn and that comprises oligosaccharides that are digestion-resistant, oligosaccharides that are slowly digestible, or a combination thereof. Soluble corn fiber can be made via corn starch hydrolysis, and contains greater than about 70% fiber and less than about 20% mono- and disaccharide sugars. The glucose units of the oligosaccharides are linked primarily by α-1,4 glycosidic bonds, but can also include α-1,6, α-1,3, and α-1,2 bonds.

In certain embodiments of the methods and compositions described herein, the soluble corn fiber has a fiber content in the range of about 70% to about 100% (w/w). In another embodiment, the fiber content of the soluble corn fiber is in the range of about 70% to about 90%, or about 70% to about 95%, or about 70% to about 100%, about 75% to about 85%, or about 75% to about 90%, or about 75% to about 95%, or about 75% to about 100%, or about 70% to about 85% (w/w). In one embodiment, the fiber content is about 70% (w/w). In another embodiment, the fiber content is about 85% (w/w). One of skill in the art will appreciate that fiber content may be measure by any suitable method known in the art, such as enzymatic gravimetry, liquid chromatography, gas-liquid chromatography, High Pressure Liquid chromatography (HPLC), High Performance Anion Exchange Chromatography with Pulsed Amperometric Detection (HPAE-PAD), and other enzymatic and chemical methods. In a preferred embodiment, the fiber content is measured by HPAE-PAD. For example, a Dionex ion chromatograph, DX500, equipped with electrochemical detector and gradient pump, is used to analyze samples that are separated on Dionex Carbopac PA1 analytical and guard columns with gradient delivery of solvents, detected using a gold electrode with a four-potential waveform, and diluted with water and passed through Amicon Ultra-4 centrifugal filter devices before analysis.

In certain embodiments of the methods and compositions described herein, the mono- and disaccharide content of the soluble corn fiber is less than about 20%. For example, in certain embodiments, the mono- and disaccharide content of the soluble corn fiber is less than about 15%, less than about 10%, less than about 5%, or even less than about 2%. In certain such embodiments, the mono- and disaccharide content of the soluble corn fiber is no less than about 0%, no less than about 0.001%, no less than about 0.01%, or even no less than 0.1%.

In certain embodiments of the methods and compositions described herein, the oligosaccharides of the soluble corn fiber have an average degree of polymerization of at least about 5, at least about 7, or at least about 9. For example, in certain embodiments of the methods and compositions described herein, the oligosaccharides of the soluble corn fiber have an average degree of polymerization in the range of about 5 to about 20, about 7 to about 20, or about 9 to about 20. In other embodiments, the oligosaccharides of the soluble corn fiber have an average degree of polymerization in the range of about 5 to about 15, about 7 to about 15, or about 9 to about 15. For example, in one embodiment the methods and compositions described herein, the oligosaccharides of the soluble corn fiber have an average degree of polymerization is about 10.

In certain embodiments of the methods and compositions described herein, the oligosaccharide portion of the soluble corn fiber remains substantially undigested in the stomach and small intestine of a subject when ingested.

Suitable commercial soluble corn fiber products include PROMITOR™ Soluble Corn Fiber 70 (minimum fiber content of about 70%, maximum mono- and disaccharide content of about 20%), and PROMITOR™ Soluble Corn Fiber 85 (minimum fiber content of about 85%, maximum mono- and disaccharide content of about 2%), available from Tate & Lyle Health & Nutrition Sciences, Hoffman Estates, Ill.

Certain soluble corn fibers suitable for use in the methods and compositions described herein are described further in U.S. Patent Applications Publications nos. 2008/0292766, 2006/0210696 and 2008/0175977, each of which is hereby incorporated herein by reference in its entirety, and which is attached in the appendix to this specification. In certain embodiments of the methods and compositions described herein, the soluble corn fiber is as described in an aspect or embodiment of U.S. Patent Application Publication no. 2008/0292766, 2006/0210696 or 2008/0175977.

Of course, as the person of ordinary skill in the art will appreciate, other fermentable soluble fibers can be used in practicing the methods and compositions as described herein. In other particular embodiments as described herein, the fermentable soluble fibers is selected from polydextrose, soluble fiber dextrin (i.e., corn, tapioca, potato starch), arabinoxylan, arabinoxylan oligosaccharides, xylose, slowly digestible (digestion resistant) carbohydrates and oligosaccharides, and functional combinations thereof, optionally in combination with soluble corn fiber. While certain embodiments of the invention are described herein with reference to soluble corn fibers, the person of ordinary skill in the art will appreciate that other fermentable soluble fibers could be used in place of the soluble corn fibers in certain embodiments of the invention.

In certain embodiments of the methods and compositions as described herein, the fermentable soluble fiber, e.g., the soluble corn fiber, is produced by a process described in U.S. Pat. Nos. 7,608,436, and 8,057,840, each of which is hereby incorporated herein by reference in its entirety. For example, in one embodiment, the process to produce the fermentable soluble fiber includes uses an aqueous feed composition that comprises at least one monosaccharide or linear saccharide oligomer, and that has a solids concentration of at least about 70% by weight. The feed composition is heated to a temperature of at least about 40° C., and is contacted with at least one catalyst that accelerates the rate of cleavage or formation of glucosyl bonds for a time sufficient to cause formation of non-linear saccharide oligomers. In one particular embodiment, the process includes heating an aqueous feed composition that comprises at least one monosaccharide or linear saccharide oligomer, and that has a solids concentration of at least about 70% by weight, to a temperature of at least about 40° C.; and contacting the feed composition with at least one catalyst that accelerates the rate of cleavage or formation of glucosyl bonds for a time sufficient to cause formation of non-linear saccharide oligomers, wherein a product composition is produced that contains a higher concentration of non-linear saccharide oligomers than linear saccharide oligomers; wherein the product composition comprises non-linear saccharide oligomers having a degree of polymerization of at least three in a concentration of at least about 20% by weight on a dry solids basis. In certain such embodiments, the product composition is produced that contains a higher concentration of non-linear saccharide oligomers than linear saccharide oligomers. In one embodiment of the process, the at least one catalyst is an enzyme that accelerates the rate of cleavage or formation of glucosyl bonds. In another embodiment of the process, the at least one catalyst is an acid. In some embodiments of the process, acid and enzyme can be used in sequence, with the feed composition first being treated with enzyme and subsequently with acid, or vice versa.

In certain embodiments of the processes as described with respect to U.S. Pat. Nos. 7,608,436, and 8,057,840, the aqueous feed composition includes at least one monosaccharide and at least one linear saccharide oligomer, and may contain several of each. In many cases, monosaccharides and oligosaccharides will make up at least about 70% by weight on a dry solids basis of the feed composition. It is generally helpful for the starting material to have as high a concentration of monosaccharides as possible, in order to maximize the yield of the desired oligomers. A high solids concentration tends to drive the equilibrium from hydrolysis toward condensation (reversion), thereby producing higher molecular weight products. Therefore the water content of the starting material is preferably relatively low. For example, in certain embodiments, the feed composition comprises at least about 75% dry solids by weight. ("Dry solids" is sometimes abbreviated herein as "ds.") In some cases, the feed composition comprises about 75-90% solids by weight, which will generally give the appearance of a viscous syrup or damp powder at room temperature.

Examples of suitable starting materials for the processes as described with respect to U.S. Pat. Nos. 7,608,436, and 8,057,840 include, but are not limited to, syrups made by hydrolysis of starch, such as dextrose greens syrup (i.e., recycle stream of mother liquor from dextrose monohydrate crystallization), other dextrose syrups, corn syrup, and solutions of maltodextrin. If the feed composition comprises maltodextrin, the process optionally can also include the steps of hydrolyzing the maltodextrin to form a hydrolyzed saccharide solution and concentrating the hydrolyzed saccharide solution to at least about 70% dry solids to form the feed composition. The concentrating and the contacting of the feed with the catalyst can occur simultaneously, or the concentrating can occur prior to contacting the feed composition with the catalyst.

In certain embodiments of the processes as described with respect to U.S. Pat. Nos. 7,608,436, and 8,057,840, the feed composition is contacted with the at least one catalyst for a period of time that can vary. In some cases, the contacting period will be at least about five hours. In some embodiments of the invention, the feed composition is contacted with the at least one catalyst for about 15-100 hours. In other embodiments, shorter contacting times can be used with higher temperatures, in some cases even less than one hour.

In certain embodiments of the processes as described with respect to U.S. Pat. Nos. 7,608,436, and 8,057,840, enzymatic reversion is used to produce nonlinear oligosaccharides. The enzyme can be, for example, one that accelerates the rate of cleavage of alpha 1-2, 1-3, 1-4, or 1-6 glucosyl bonds to form dextrose residues. One suitable example is a glucoamylase enzyme composition, such as a commercial enzyme composition that is denominated as a glucoamylase. It should be understood that such a composition can contain some quantity of enzymes other than pure glucoamylase, and it should not be assumed that it is in fact glucoamylase itself that catalyzes the desired production of nonlinear oligosaccharides. Therefore, the feed composition can be contacted with glucoamylase or any other enzyme that acts on dextrose polymers. The amount of enzyme can suitably be about 0.5-2.5% by volume of the feed composition. In some embodiments of the process, the feed composition is maintained at about 55-75° C. during the contacting with the enzyme, or in some cases about 60-65° C. At this temperature, depending on the water content, the material will become a liquid, or a mixture of liquid and solid. Optionally, the reaction mixture can be mixed or agitated to distribute the enzyme. The reaction mixture is maintained at the desired temperature for the time necessary to achieve the desired degree of reversion to non-linear oligomers. In some embodiments of the process, the feed composition is contacted with the enzyme for about 20-100 hours prior to inactivation of the enzyme, or in some cases, for about 50-100 hours prior to inactivation. Techniques for inactivating glucoamylase are well known in the field. Alternatively, instead of inactivating the enzyme, it can be separated by membrane filtration and recycled.

In certain embodiments of the processes as described with respect to U.S. Pat. Nos. 7,608,436, and 8,057,840, the resulting composition has a high concentration of non-linear oligosaccharides, such as isomaltose. This product composition contains a higher concentration of non-linear saccharide oligomers than linear saccharide oligomers. In some cases, the concentration of non-linear saccharide oligomers in the final composition is at least twice as high as the concentration of linear saccharide oligomers.

Another embodiment processes as described with respect to U.S. Pat. Nos. 7,608,436, and 8,057,840 involves acid reversion of monosaccharides. The starting material is the same as described above with respect to the enzyme version of the process. A variety of acids can be used, such as hydrochloric acid, sulfuric acid, phosphoric acid, or a combination thereof. In some embodiments of the process, acid is added to the feed composition in an amount sufficient to make the pH of the feed composition no greater than about 4, or in some cases, in an amount sufficient to make the pH of the feed composition about 1.0-2.5, or about 1.5-2.0. In some embodiments, the solids concentration of the feed composition is about 70-90%, the amount of acid added to the feed is about 0.05%-0.25% (w/w) acid solids on syrup dry solids, and the feed composition is maintained at a temperature of about 70-90° C. during the contacting with the acid. As in the enzyme version of the process, the reaction conditions are maintained for a time sufficient to produce the desired oligomers, which in some embodiments of the process will be about 4-24 hours.

In one particular embodiment of the processes described with respect to U.S. Pat. Nos. 7,608,436, and 8,057,840, the solids concentration of the feed composition is at least about 80% by weight, acid is added to the feed composition in an amount sufficient to make the pH of the composition about 1.8, and the feed composition is maintained at a temperature of at least about 80° C. for about 4-24 hours after it is contacted with the acid.

In another particular embodiment of the processes described with respect to U.S. Pat. Nos. 7,608,436, and 8,057,840, the solids concentration of the feed composition is about 90-100% by weight, and the feed composition is maintained at a temperature of at least about 149° C. (300° F.) for about 0.1-15 minutes after it is contacted with the acid. The acid used to treat the feed can be a combination of phosphoric acid and hydrochloric acid (at the same concentrations discussed above). In one particular embodiment, the contacting of the feed composition with the acid takes place in a continuous pipe/flow through reactor.

By far the most plentiful glycosidic linkage in starch is the alpha-1,4 linkage, and this is the linkage most commonly broken during acid hydrolysis of starch. But acid-catalyzed reversion (condensation) can take place between any two hydroxyl groups, and, given the large variety of combinations and geometries available, the probability of an alpha-1,4 linkage being formed is relatively small. The human digestive system contains alpha amylases which readily digest the alpha-1,4 linkages of starch and corn syrups. Replacing these linkages with linkages unrecognized by enzymes in the digestive system will allow the product to pass through to the small intestines largely unchanged. The saccharide distributions resulting from acid treatment are believed to be somewhat different than from enzyme treatment. It is believed that these acid-catalyzed condensation products will be less recognizable by the enzymes in the human gut than enzyme-produced products, and therefore less digestible.

The acid treatment progresses differently than enzyme treatment. Enzymes rapidly hydrolyze linear oligomers and slowly form non-linear oligomers, whereas with acid the reduction in linear oligomers and the increase in non-linear oligomers occur at comparable rates. Dextrose is formed rapidly by enzymatic hydrolysis of oligomers, and consumed slowly as non-linear condensation products are formed, whereas with acid dextrose concentrations increase slowly.

Optionally, in certain embodiments of the processes described with respect to U.S. Pat. Nos. 7,608,436, and 8,057,840, enzymatic or acid reversion can be followed by hydrogenation. The hydrogenated product should have lower caloric content than currently available hydrogenated starch hydrolysates. In one embodiment, the hydrogenation can be used to decolorize the product composition without substantially changing its dextrose equivalence (DE). In one version of the process, enzyme and acid can be used sequentially, in any order. For example, the at least one catalyst used in the first treatment can be enzyme, and the product composition can be subsequently contacted with an acid that accelerates the rate of cleavage or formation of glucosyl bonds. Alternatively, the at least one catalyst used in the first treatment can be acid, and the product composition can be subsequently contacted with an enzyme that accelerates the rate of cleavage or formation of glucosyl bonds.

The product composition produced by the treatment with acid, enzyme, or both, has an increased concentration on a dry solids basis of non-linear saccharide oligomers. In some cases, the concentration of non-linear saccharide oligomers having a degree of polymerization of at least three (DP3+) in the product composition is at least about 20%, at least about 25%, at least about 30%, or at least about 50% by weight on a dry solids basis. In certain such embodiments, the concentration of non-linear saccharide oligomers having a degree of polymerization of at least three (DP3+) in the product composition is no more than about 100%, or no more than about 99%, or no more than about 95%, or no more than about 90% by weight on a dry solids basis. In some embodiments, the concentration of non-linear saccharide oligomers in the product composition is at least twice as high as the concentration of linear saccharide oligomers.

In one particular embodiment of the processes described with respect to U.S. Pat. Nos. 7,608,436, and 8,057,840, the concentration of non-linear saccharide oligomers in the product composition is at least about 90% by weight on a dry solids basis, and the concentration of isomaltose is at least about 70% by weight on a dry solids basis.

The product composition will often contain some quantity (typically less than 50% by weight on a dry solids basis, and often much less) of residual monosaccharides. Optionally, at least some of the residual monosaccharides (and other species) can be separated from the oligomers (for example by membrane filtration, chromatographic separation, or digestion via fermentation) and the monosaccharide stream can be recycled into the process feed. In this way, simple sugar syrups can be converted to high-value food additives.

FIG. 1 shows one embodiment of a process which can make use of the reversion technique described above. The process can begin with a starch, for example a vegetable starch. Conventional corn starch is one suitable example. The process will generally operate more efficiently if the beginning starch has a relatively high purity. In one embodiment, the high purity starch contains less than 0.5% protein on a dry solids basis. Although some of the following discussion focuses on corn, it should be understood that the present invention is also applicable to starches derived from other sources, such as potato and wheat, among others.

Figure 9:
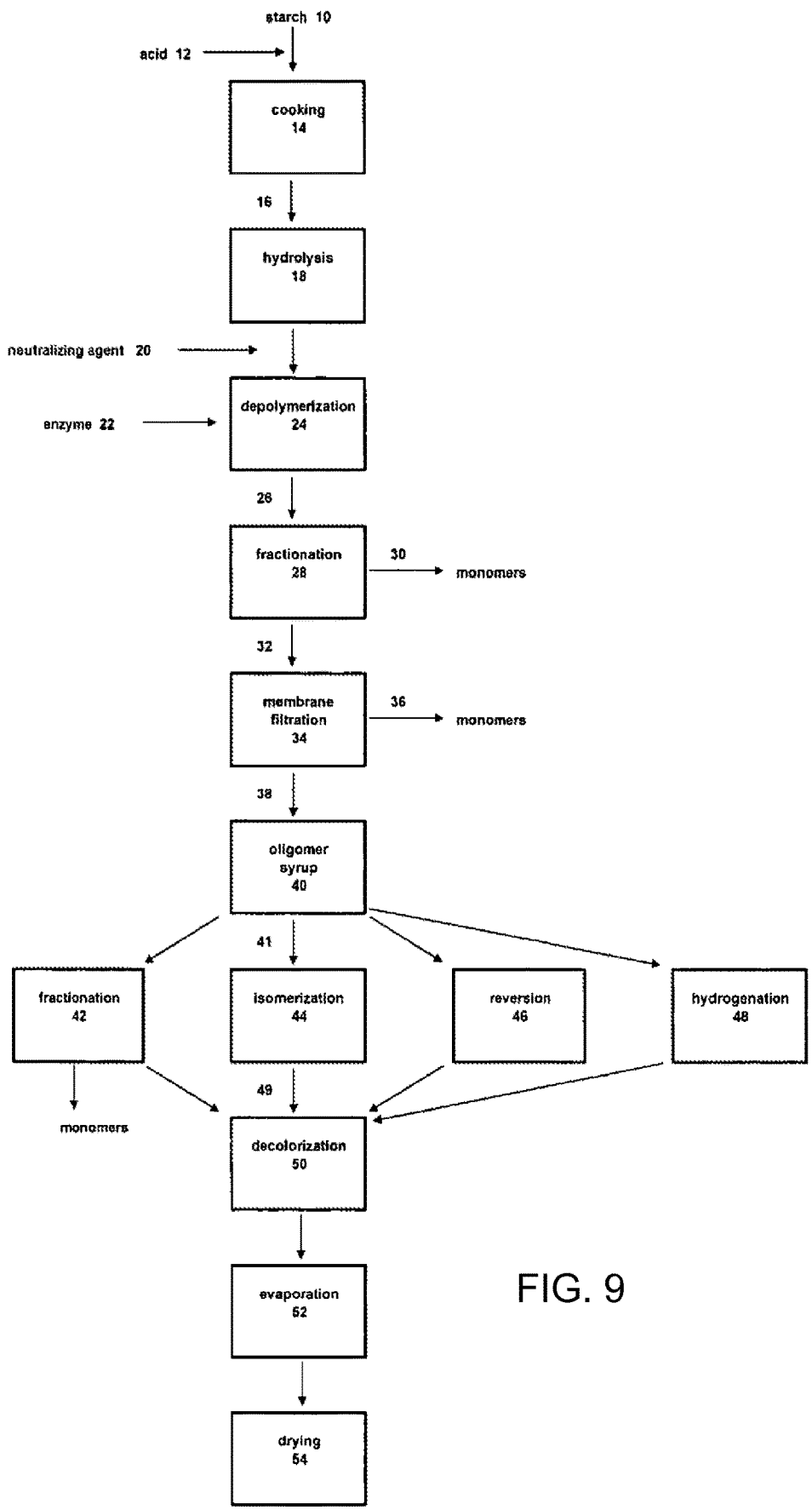
FIG. 9 is a schematic diagram demonstrating an example of a method for making fermentable soluble fiber.

Certain embodiments of the processes as described herein with respect to U.S. Pat. Nos. 7,608,436, and 8,057,840 are illustrated schematically in FIG. 9. As shown in FIG. 9, the starch 10 can have acid 12 added to it and can then be gelatinized 14 in a starch cooker, for example in a jet cooker in which starch granules are contacted with steam. In one version of the process, the starch slurry, adjusted to a pH target of 3.5 by addition of sulfuric acid, is rapidly mixed with steam in a jet cooker and held at 149 to 152° C. (300 to 305° F.) for 4 minutes in a tail line. The gelatinized starch 16 is hydrolyzed 18 by exposure to acid at high temperature during jet cooking. The hydrolysis reduces the molecular weight of the starch and generates an increased percentage of monosaccharides and oligosaccharides in the composition. (As mentioned above, the term "oligosaccharides" is used herein to refer to saccharides comprising at least two saccharide units, for example saccharides having a degree of polymerization (DP) of about 2-30.) A neutralizing agent 20, such as sodium carbonate, can be added to stop the acid hydrolysis, and then the composition can be further depolymerized 24 by contacting it with a hydrolytic enzyme 22. Suitable enzymes include alpha amylases such as Termamyl, which is available from Novozymes. This enzymatic hydrolysis further increases the percentage of monosaccharides and oligosaccharides present in the composition. The overall result of the hydrolysis by acid and enzyme treatment is to saccharify the starch. The saccharified composition can be isomerized to change the monosaccharide profile, for example to increase the concentration of fructose.

The saccharified composition 26 can then be purified, for example by chromatographic fractionation 28. In one embodiment that employs a sequential simulated moving bed (SSMB) chromatography procedure, a solution of mixed saccharides is pumped through a column filled with resin beads. Depending on the chemical nature of the resin, some of the saccharides interact with the resin more strongly leading to a retarded flow through the resin compared to saccharides that interact with the resin more weakly. This fractionation can produce one stream 30 that has a high content of monosaccharides, such as dextrose and fructose. High fructose corn syrup is an example of such a stream. The fractionation also produces a raffinate stream 32 (i.e., faster moving components through the resin bed) that has a relatively high concentration of oligosaccharides (e.g., about 5-15% oligosaccharides on a dry solids basis (d.s.b.)) and also contains a smaller concentration of monosaccharides such as dextrose and fructose. Although the term "stream" is used herein to describe certain parts of the process, it should be understood that the process of the present invention is not limited to continuous operation. The process can also be performed in batch or semi-batch mode.

The raffinate 32 can be further fractionated by membrane filtration 34, for example by nanofiltration, optionally with diafiltration. For example, these filtration steps can be performed using a Desal DK spiral wound nanofiltration cartridge at about 500 psi of pressure and at 40-60 degrees centigrade temperature. The fractionation described in step 34 could also be accomplished by sequential simulated moving bed chromatography (SSMB). The membrane filtration produces a permeate 36 (i.e., components that pass through the membrane) which comprises primarily monosaccharides, and a retentate 38 (i.e., components rejected by the membrane) which comprises primarily oligosaccharides. ("Primarily" as used herein means that the composition contains more of the listed component than of any other component on a dry solids basis.) The permeate 36 can be combined with the monomer stream 30 (e.g., high fructose corn syrup). The permeate is a monosaccharide-rich stream and the retentate is an oligosaccharide-rich stream. In other words, the nanofiltration concentrates the oligosaccharides in the retentate and the monosaccharides in the permeate, relative to the nanofiltration feed.

The retentate 38, which can be described as an oligosaccharide syrup 40, can have a sufficiently high content of oligosaccharides that are slowly digestible (e.g., at least about 50% by weight d.s.b., or in some cases at least about 90%) so that it can be dried or simply evaporated to a concentrated syrup and used as an ingredient in foods. However, in many cases, it will be useful to further process and purify this composition. Such purification can include one or more of the following steps. (Although FIG. 9 shows four such purification steps 42, 44, 46, and 48 as alternatives, it should be understood that two or more of these steps could be used in the process.)

The oligomers syrup 40 can be subjected to another fractionation 42, such as a membrane filtration, for example a second nanofiltration, in order to remove at least some of the residual monosaccharides, such as fructose and dextrose. Suitable nanofiltration conditions and equipment are as described above. This nanofiltration produces a permeate, which is a second monosaccharide-rich stream, which can be combined with the monomer stream 30. Alternatively, the further fractionation 42 could be done by chromatographic separation, for example, by simulated mixed-bed chromatography.

The syrup 41 can be isomerized 44 by contacting it with an enzyme such as dextrose isomerase. This will convert at least some of the residual dextrose present into fructose, which may be more valuable in certain situations.

The syrup can be treated with an enzyme or acid to cause reversion or repolymerization 46, in which at least some of the monosaccharides that are still present are covalently bonded to other monosaccharides or to oligosaccharides, thereby reducing the residual monomer content of the syrup even further. Suitable enzymes for use in this step include glucosidases, such as amylase, glucoamylase, transglucosidase, and pullulanase. Cellulase enzymes may produce valuable reversion products for some applications.

The syrup can be hydrogenated 48 to convert at least some of any residual monosaccharides to the corresponding alcohols (e.g., to convert dextrose to sorbitol). When hydrogenation is included in the process, it will typically (but not necessarily) be the final purification step.

The purified oligomer syrup 49 produced by one or more of the above purification steps can then be decolorized 50. Decolorization can be done by treatment with activated carbon followed by microfiltration, for example. In continuous flow systems, syrup streams can be pumped through columns filled with granular activated carbon to achieve decolorization. The decolorized oligomer syrup can then be evaporated 52, for example to about greater than about 70% dry solids (d.s.), giving a product that comprises a high content of oligosaccharides (e.g., greater than 90% by wt d.s.b., and in some instances greater than 95%), and a correspondingly low monosaccharide content. The product comprises a plurality of saccharides which are slowly or incompletely digested by humans, if not totally indigestible.

These sugars can include isomaltose, panose and branched oligomers having a degree of polymerization of four or greater.

The process conditions can be modified to recover the majority of the maltose in the feed either in the monomer-rich streams (30, 36) or in the oligomer product stream. For example, a nanofiltration membrane with a slightly larger pores, such as Desal DL, operating at less than 500 psi pressure can be used to increase the amount of maltose in monomer-rich streams.

In certain embodiments of the methods and compositions as described herein, the fermentable soluble fiber is a slowly digestible saccharide oligomer composition that is suitable for use in foods. "Slowly digestible" as the term is used herein means that one or more carbohydrates are either not digested at all in the human stomach and small intestine, or are only digested to a limited extent. Both in vitro and in vivo tests can be performed to estimate the rate and extent of carbohydrate digestion in humans. The "Englyst Assay" is an in vitro enzyme test that can be used to estimate the amounts of a carbohydrate ingredient that are rapidly digestible, slowly digestible or resistant to digestion (European Journal of Clinical Nutrition (1992) Volume 46 (Suppl. 2), pages S33-S50). Thus, any reference herein to "at least about 50% by weight on a dry solids basis" of a material being "slowly digestible" means that the sum of the percentages of that material that are classified as slowly digestible or as resistant by the Englyst assay totals at least about 50%. The terms "oligosaccharides" and "saccharide oligomers" are used herein to refer to saccharides comprising at least two saccharide units, for example saccharides having a degree of polymerization ("DP") of about 2-30. For example, a disaccharide has a DP of 2.

Gastrointestinal enzymes readily recognize and digest carbohydrates in which the dextrose units are linked alpha (1→4) ("linear" linkages). Replacing these linkages with alternative linkages (alpha (1→3), alpha (1→6) ("non-linear" linkages) or beta linkages, for example) greatly reduces the ability of gastrointestinal enzymes to digest the carbohydrate. This will allow the carbohydrates to pass on into the small intestines largely unchanged. In certain embodiments of the methods and compositions as described herein, the fermentable soluble fiber, e.g., the soluble corn fiber, comprises a minor amount (i.e., less than 50 wt % on a dry solids basis, and usually a much lower concentration, e.g., less than 40 wt %, less than 30 wt %) of residual monosaccharides. In some embodiments as described herein, at least about 50% by weight on a dry solids basis of the product composition is slowly digestible. The processes as described with respect to U.S. Pat. Nos. 7,608,436, and 8,057,840 can include the additional step of removing at least some of the residual monosaccharides (and optionally other species as well) from the product composition by membrane filtration, chromatographic fractionation, or digestion via fermentation. The separated monosaccharides can be combined with other process streams, for example for production of dextrose or corn syrup. Alternatively, the separated monosaccharides can be recycled into the feed composition.

In certain embodiments of the methods and compositions as described herein, the fermentable soluble fiber comprises a major amount (e.g., greater than 50%, greater than about 60%, or greater than about 70%) on a dry solids basis of linear and non-linear saccharide oligomers, and wherein the concentration of non-linear saccharide oligomers is greater than the concentration of linear saccharide oligomers, and wherein the concentration of non-linear saccharide oligomers having a degree of polymerization of at least three is at least about 20% by weight on a dry solids basis. For example, in certain embodiments, the concentration of non-linear saccharide oligomers in the composition is at least twice as high as the concentration of linear saccharide oligomers. In certain embodiments, the concentration of non-linear saccharide oligomers having a degree of polymerization of at least three is at least about 25% by weight on a dry solids basis. In certain embodiments, the concentration of non-linear saccharide oligomers having a degree of polymerization of at least three is at least about 30% by weight, or even at least 50% by weight, on a dry solids basis. In certain embodiments, wherein the concentration of non-linear saccharide oligomers is at least about 90% by weight on a dry solids basis, and the concentration of isomaltose is at least about 70% by weight on a dry solids basis.

In certain embodiments of the methods and compositions described herein, the fermentable soluble fiber, e.g., soluble corn fiber, is administered at a rate of at least about 3 g/day. For example, in certain embodiments, the fermentable soluble fiber, e.g., soluble corn fiber, is administered at a rate of at least about 5 g/day, at least about 7 g/day, at least about 10/day, at least about 12 g/day, at least about 13 g/day, at least about 15 g/day, or even at least about 20 g/day and no more than about 100 g/day, or no more than 75 g/day. Specifically, clinically relevant gastrointestinal tolerance has been established at 65 g/day when spread over 12 hrs (a normal eating day) and/or at 40 g/acute bolus day. These are both well tolerated doses. Accordingly, in certain such embodiments, the fermentable soluble fiber, e.g., soluble corn fiber, is administered at a rate of no more than about 65 g over 12 hours, and/or no more than about 40 g in a single bolus.

For example, in certain embodiments of the methods and compositions described herein, the fermentable soluble fiber, e.g., soluble corn fiber, is administered at a rate in the range of about 3 g/day to about 100 g/day. In other embodiments of the methods and compositions described herein, the fermentable soluble fiber, e.g., soluble corn fiber, is administered at a rate in the range of about 10 g/day to about 100 g/day, or about 12 g/day to about 100 g/day. In other embodiments of the methods and compositions described herein, the fermentable soluble fiber, e.g., soluble corn fiber, is administered at a rate in the range of about 5 to about 65 g/day, about 5 to about 40 g/day, about 5 to about 30 g/day, about 5 to about 20 g/day, about 10 to about 65 g/day, about 10 to about 40 g/day, about 10 to about 30 g/day, about 15 to about 65 g/day, about 15 to about 40 g/day, about 15 to about 30 g/day, about 5 to about 15 g/day, about 7 to about 15 g/day, about 9 to about 15 g/day, or about 10 to about 15 g/day, about 12 to about 20 g/day, about 13 to about 20 g/day, about 14 to about 20 g/day, about 15 to about 20 g/day, about 16 to about 20 g/day, about 17 to about 20 g/day, about 18 to about 20 g/day, or about 19 to about 20 g/day. In certain embodiments of the methods and compositions described herein, the fermentable soluble fiber, e.g., soluble corn fiber, is administered at a rate of about 5 g/day, about 6 g/day, about 7 g/day, about 8 g/day, about 9 g/day, or about 10 g/day. In other embodiments of the methods and compositions described herein, the fermentable soluble fiber, e.g., soluble corn fiber, is administered at a rate in the range of about 11 to about 20 g/day. In other embodiments of the methods and compositions described herein, the fermentable soluble fiber, e.g., soluble corn fiber, is administered at a rate of about 11 g/day, or about 12 g/day, or about 13 g/day, or about 14 g/day, or about 15 g/day, or about 16 g/day, or about 17 g/day, or about 18 g/day, or about 19 g/day, or about 20 g/day.

In a given day, the administration can be broken up into any number of dosages. For example, in one embodiment of the methods and compositions described herein, th the fermentable soluble fiber, e.g., soluble corn fiber, is administered once per day (e.g., in a single serving). In other embodiments of the methods and compositions described herein, the fermentable soluble fiber, e.g., soluble corn fiber, is administered a plurality of times a day, for example, twice per day or three times per day (e.g., in a plurality of servings, for example, in two servings or in three servings per day). When a plurality of administrations or servings is to be used, the amounts per day described above can be divided among the number of administrations or servings to provide acceptable amounts per serving that are well tolerated (i.e., does not cause severe bloating, flatulence, stomach noises, abdominal cramps, diarrhea, nausea, and/or vomiting).

In another aspect, the disclosure provides a method of increasing mineral (e.g., calcium, iron, zinc, copper, potassium and/or magnesium) absorption in a subject, where the method includes orally administering to the subject a fermentable soluble fiber, e.g., soluble corn fiber. In certain such embodiments, the mineral for which absorption is increased is a mineral, such as, for example calcium and/or iron. In certain embodiments of the methods and compositions as described herein, the mineral is absorbed as a divalent cation. In certain embodiments of the methods and compositions as described herein, the mineral is calcium. In other embodiments of the methods and compositions as described herein, the mineral is calcium and/or magnesium. In certain embodiments of the methods and compositions as described herein, the mineral is calcium and/or iron. In other embodiments of the methods and compositions as described herein, the mineral is calcium, magnesium and/or iron. The administration can, in certain embodiments, be as otherwise described herein.

In another embodiment, the disclosure provides a method of increasing one or more colonic bacteria populations and increasing mineral (e.g., calcium, iron, zinc, copper, potassium and/or magnesium) absorption in a subject, where the method includes orally administering to a fermentable soluble fiber, e.g., soluble corn fiber. The administration can, in certain embodiments, be as otherwise described herein.

In certain embodiments of the methods and compositions described herein, calcium absorption is increased by at least about 3% as compared to a non-treated subject. In certain embodiments of the methods and compositions described herein, calcium absorption is increased by at least about 5%, at least about 6%, at least about 7%, at least about 8%, at least about 9%, at least about 10%, at least about 11%, at least about 12%, at least about 13%, or at least about 14%, or at least about 15%, as compared to the non-treated subject. In other embodiments of the methods and compositions described herein, calcium absorption is increased by at least about 20%, or at least about 25% as compared to a non-treated subject. In certain embodiments of the methods and compositions described herein, calcium absorption is increased by at least about 20%, at least about 25%, at least about 30%, or at least about 35% as compared to a non-treated subject. In certain such embodiments, calcium absorption is increased by no more than about 200% as compared to a non-treated subject. In other such embodiments, calcium absorption is increased by no more than about 100% as compared to a non-treated subject. In other such embodiments, calcium absorption is increased by no more than about 50% as compared to a non-treated subject. The timing for calcium absorption can be, for example, in the range of 24-48 h, e.g., at 36 h or 48 h.

In certain embodiments of the methods and compositions described herein, the subject is a mammal. In one embodiment of the methods and compositions described herein, the subject is a human, for example, a non-adult human (e.g., in the range of about 2 years old to about 20 years old, or about 13 years old to about 19 years old), or an older human (e.g., at least about 45 years old, at least about 50 years old, at least about 60 years old, at least about 70 years old, at least about 80 years old or even at least about 90 years old, especially an older female human). Accordingly, in certain embodiments the methods and compositions described herein can be used with subjects who are especially likely to benefit from increased mineral (e.g., calcium) absorption.

It is envisioned that the effects of increasing one or more colonic bacteria populations and/or increasing calcium absorption relate to both humans and animals, and thus can be applied to foodstuffs and animal feed. Representative non-human animals include, livestock, such as horses, chicken, turkeys, cattle, cow, swine, sheep, goats, llamas and bison, cats and dogs, rodents, rabbits, hamsters and birds.

The administration can be performed over an extended time period, for example, over the course of at least about a week, over the course of at least about two weeks, of at least about three weeks over the course of at least about four weeks, of at least about seven weeks or even over the course of at least about 52 weeks. The person of ordinary skill in the art that in such long-term administrations, days of administration may be "missed"; desirably the number of days missed is less than about 10% of the total number of days over which the administration is performed.

Another embodiment of the invention is an edible composition that includes at least about 2.5 g of fermentable soluble fiber, e.g., soluble corn fiber, per serving. For example, certain embodiments of edible compositions as described herein include at least about 3 g, at least about 4 g, at least about 5 g, at least about 6 g, at least about 8 g, at least about 10 g, or even at least about 20 g of fermentable soluble fiber, e.g., soluble corn fiber, per serving. In certain such embodiments, the edible composition includes no more than 100 g, no more than about 50 g, or even no more than about 40 g of fermentable soluble fiber, e.g., soluble corn fiber, per serving. The edible compositions can, for example, be provided as food compositions as described below. In other embodiments, an edible composition is provided as a nutritional supplement. Such edible compositions can be useful in performing the methods described herein.

In certain such embodiments of the compositions as described herein, the size of the serving can be, for example, at least about 75 g, at least about 150 g, or even at least about 200 g. In certain embodiments, the size of the serving is no more than about 1000 g, or even no more than about 500 g. For example, in one embodiment, the serving size in the range of about 75 mL to about 1000 mL. In certain embodiments, each serving is separately packaged. In other embodiments, multiple servings are packaged together, and provided with instructions relating a serving size and/or an amount of fermentable soluble fiber, e.g., soluble corn fiber, per serving as described herein.

Another embodiment of the invention is an edible composition that includes fermentable soluble fiber, e.g., soluble corn fiber, in an amount of at least about 2.5%, at least about 3%, at least about 5%, at least about 10%, at least about 20%, at least about 30%, or even at least about 40% by weight. However, in certain such embodiments, the edible composition has a maximum amount of fermentable soluble fiber, e.g., soluble corn fiber, that is no greater than about 75%, or even no greater than about 50% by weight. The edible compositions can, for example, be provided as food compositions as described below. The edible compositions can, for example, be provided with the serving sizes and/or the amounts of soluble corn fiber per serving as described herein.

Another embodiment of the invention is an edible composition that includes one or more (e.g., two or more, or three or more) bacterial populations, each from a genus selected from the group consisting of *Lactobacillus, Bacteroides, Parabacteroides, Alistipes, Bifidobacterium, Butyricicoccus, Oscillibacter*, and *Dialister*, as well as the bacteria indicated as increasing in population with soluble corn fiber administration in Table 5, and the bacteria indicated as being correlated with calcium absorption in Table 6. One or more of the bacterial populations, can, for example, act as probiotics. The edible compositions described herein can, in certain embodiments, include fermentable soluble fiber, e.g., soluble corn fiber, (for example, in an amount as described above). But in other embodiments, the edible composition does not include a fermentable soluble fiber. Such embodiments can be useful, for example, for addition to or co-administration with compositions including fermentable soluble fibers, such that the bacterial populations of the edible composition are present in the colon at the same time as the fermentable soluble fiber. Accordingly, the subject can in certain embodiments enjoy the benefits of the combination of fermentable soluble fibers with the bacterial populations identified herein without being administered a single composition that includes both the fermentable soluble fibers and the bacterial populations. Similarly, products suitable for the enjoyment the benefits of the combination of the fermentable soluble fibers with the bacterial populations identified herein can be formulated that do not include both the fermentable soluble fiber and the bacterial populations.

For example, in certain embodiments of the edible compositions described herein, the edible composition includes one or more (e.g., two or more, or three or more) bacteria populations, each from a genus (e.g., each from a different genus) selected from the group consisting of *Parabacteroides, Butyricicoccus, Oscillibacter*, and *Dialister*, and any combination thereof. For example, one embodiment of the edible compositions described herein includes a population of *Parabacteroides*. Another embodiment of the edible compositions described herein includes a population of *Butyricicoccus*. Another embodiment of the edible compositions described herein includes a population of *Oscillibacter*. Another embodiment of the edible compositions described herein includes a population of *Dialister*. For example, certain embodiments of the edible compositions described herein include populations of *Parabacteroides* and *Butyricicoccus; Parabacteroides* and *Oscillibacter; Parabacteroides* and *Dialister; Butyricicoccus* and *Oscillibacter; Butyricicoccus* and *Dialister; Oscillibacter* and *Dialister; Parabacteroides, Butyricicoccus* and *Oscillibacter; Parabacteroides, Butyricicoccus* and *Dialister; Parabacteroides, Oscillibacter*, and *Dialister; Butyricicoccus, Oscillibacter*, and *Dialister;* or *Parabacteroides, Butyricicoccus, Oscillibacter*, and *Dialister.*

In other embodiments of the edible compositions described herein, the edible composition includes one or more (e.g., two or more, or three or more) bacteria populations, each from a genus (e.g., each from a different genus) selected from the group consisting of *Bacteroides, Butyricicoccus, Oscillibacter*, and *Dialister*, and any combination thereof. For example, one embodiment of the edible compositions described herein includes a population of *Bacteroides*. Another embodiment of the edible compositions described herein includes a population of *Butyricicoccus*. Another embodiment of the edible compositions described herein includes a population of *Oscillibacter*. Another embodiment of the edible compositions described herein includes a population of *Dialister*. For example, certain embodiments of the edible compositions described herein include populations of *Bacteroides* and *Butyricicoccus; Bacteroides* and *Oscillibacter; Bacteroides* and *Dialister; Butyricicoccus* and *Oscillibacter; Butyricicoccus* and *Dialister; Oscillibacter* and *Dialister; Bacteroides, Butyricicoccus* and *Oscillibacter; Bacteroides, Butyricicoccus* and *Dialister; Parabacteroides, Oscillibacter*, and *Dialister; Butyricicoccus, Oscillibacter*, and *Dialister;* or *Parabacteroides, Butyricicoccus, Oscillibacter*, and *Dialister.*

In other embodiments of the edible compositions described herein, the edible composition includes one or more (e.g., two or more, or three or more) bacteria populations, each from a genus (e.g., each from a different genus) selected from the group consisting of *Parabacteroides, Bifidobacterium, Alistipes, Anaerococcus, Catenibacterium*, genera within the order Clostridiales (e.g., not *Clostridium, Anaerofustis, Anaerococcus, Coprococcus, Peptostreptococcaceae, Sporacetigenium*); and genera within the family Ruminococcaceae and any combination thereof. For example, one embodiment of the edible compositions described herein includes a population of *Parabacteroides*. Another embodiment of the edible compositions described herein includes a population of *Bifidobacterium*. Another embodiment of the edible compositions described herein includes a population of *Alistipes*. Another embodiment of the edible compositions described herein includes a population of *Anaerococcus*. Another embodiment of the edible compositions described herein includes a population of *Catenibacterium*. Another embodiment of the edible compositions described herein includes a population of Ruminococcaceae. Another embodiment of the edible compositions described herein includes a population of Clostridiales. For example, certain embodiments of the edible compositions described herein include populations of *Parabacteroides* and *Bifidobacterium; Parabacteroides* and *Alistipes; Parabacteroides* and *Anaerococcus; Parabacteroides* and *Catenibacterium; Parabacteroides* and Ruminococcaceae; *Parabacteroides* and Clostridiales; *Bifidobacterium* and *Alistipes; Bifidobacterium* and *Anaerococcus; Bifidobacterium* and *Catenibacterium; Bifidobacterium* and Ruminococcaceae; *Bifidobacterium* and Clostridiales; *Alistipes* and *Anaerococcus; Alistipes* and *Catenibacterium; Alistipes* and Ruminococcaceae; *Anaerococcus* and *Catenibacterium; Anaerococcus* and Ruminococcaceae; *Anaerococcus* and Clostridiales; *Catenibacterium* and Ruminococcaceae; *Catenibacterium* and Clostridiales; Ruminococcaceae and Clostridiales; *Parabacteroides, Bifidobacterium* and *Alistipes; Parabacteroides, Bifidobacterium* and *Anaerococcus; Parabacteroides, Bifidobacterium* and *Catenibacterium; Parabacteroides, Bifidobacterium* and Clostridiales; *Parabacteroides, Bifidobacterium* and Ruminococcaceae; *Parabacteroides, Alistipes* and *Anaerococcus; Parabacteroides, Alistipes* and *Catenibacterium; Parabacteroides, Alistipes* and Clostridiales; *Parabacteroides, Alistipes* and Ruminococcaceae; *Parabacteroides, Anaerococcus* and *Catenibacterium; Parabacteroides, Anaerococcus* and Clostridiales; *Parabacteroides, Anaerococcus* and Ruminococcaceae; *Parabacteroides, Catenibacterium* and Clostridiales; *Parabacteroides, Catenibacterium* and Ruminococcaceae; *Parabacteroides,* Clostridiales and Ruminococcaceae; *Bifidobacterium, Alistipes* and *Anaerococcus; Bifidobacterium, Alistipes* and *Catenibacterium; Bifidobacterium, Alistipes* and Clostridiales; Bifidobacterium, Alistipes and Ruminococcaceae; Bifidobacterium, Anaerococcus and Catenibacterium; Bifidobacterium, Anaerococcus and Clostridiales; Bifidobacterium, Anaerococcus and Ruminococcaceae; Bifidobacterium, Catenibacterium and Clostridiales; Bifidobacterium, Catenibacterium and Ruminococcaceae; Bifidobacterium, Clostridiales and Ruminococcaceae; Alistipes, Anaerococcus and Catenibacterium; Alistipes, Anaerococcus and Clostridiales; Alistipes, Anaerococcus and Ruminococcaceae; Alistipes, Catenibacterium and Clostridiales; Alistipes, Catenibacterium and Ruminococcaceae; Alistipes, Clostridiales and Ruminococcaceae; Anaerococcus, Catenibacterium and Clostridiales; Anaerococcus, Catenibacterium and Ruminococcaceae; Anaerococcus, Clostridiales and Ruminococcaceae; Catenibacterium, Clostridiales and Ruminococcaceae; Parabacteroides, Bifidobacterium, Alistipes and Anaerococcus; Parabacteroides, Bifidobacterium, Alistipes and Catenibacterium; Parabacteroides, Bifidobacterium, Alistipes and Clostridiales; Parabacteroides, Bifidobacterium, Alistipes and Ruminococcaceae; Parabacteroides, Bifidobacterium, Anaerococcus and Catenibacterium; Parabacteroides, Bifidobacterium, Anaerococcus and Clostridiales; Parabacteroides, Bifidobacterium, Anaerococcus and Ruminococcaceae; Parabacteroides, Bifidobacterium, Catenibacterium and Clostridiales; Parabacteroides, Bifidobacterium, Catenibacterium and Ruminococcaceae; Parabacteroides, Bifidobacterium, Clostridiales and Ruminococcaceae; Parabacteroides, Alistipes, Anaerococcus and Catenibacterium; Parabacteroides, Alistipes, Anaerococcus and Clostridiales; Parabacteroides, Alistipes, Anaerococcus and Ruminococcaceae; Parabacteroides, Alistipes, Catenibacterium and Clostridiales; Parabacteroides, Alistipes, Catenibacterium and Ruminococcaceae; Parabacteroides, Alistipes, Clostridiales and Ruminococcaceae; Parabacteroides, Anaerococcus, Catenibacterium and Clostridiales; Parabacteroides, Anaerococcus, Catenibacterium and Ruminococcaceae; Parabacteroides, Anaerococcus, Clostridiales and Ruminococcaceae; Parabacteroides, Catenibacterium, Clostridiales and Ruminococcaceae; Bifidobacterium, Alistipes, Anaerococcus and Catenibacterium; Bifidobacterium, Alistipes, Anaerococcus and Clostridiales; Bifidobacterium, Alistipes, Anaerococcus and Ruminococcaceae; Bifidobacterium, Alistipes, Catenibacterium and Clostridiales; Bifidobacterium, Alistipes, Catenibacterium and Ruminococcaceae; Bifidobacterium, Alistipes, Clostridiales and Ruminococcaceae; Bifidobacterium, Anaerococcus, Catenibacterium and Clostridiales; Bifidobacterium, Anaerococcus, Catenibacterium and Ruminococcaceae; Bifidobacterium, Anaerococcus, Clostridiales and Ruminococcaceae; Bifidobacterium, Catenibacterium, Clostridiales and Ruminococcaceae; Alistipes, Anaerococcus, Catenibacterium and Clostridiales; Alistipes, Anaerococcus, Catenibacterium and Ruminococcaceae; Alistipes, Anaerococcus, Clostridiales and Ruminococcaceae; Alistipes, Catenibacterium, Clostridiales and Ruminococcaceae; or Anaerococcus, Catenibacterium, Clostridiales and Ruminococcaceae. Of course, the person of ordinary skill in the art will appreciate that any combination of 5, 6, or 7 colonic bacteria populations, each from a different genus selected from the group consisting of Parabacteroides, Bifidobacterium, Alistipes, Anaerococcus, Catenibacterium, genera within the order Clostridiales; and genera within the family Ruminococcaceae, may be included in the edible compositions described herein.

In other embodiments of the edible compositions described herein, the edible composition includes one or more (e.g., two or more, or three or more) bacteria populations, each from a genus (e.g., each from a different genus) selected from the group consisting of Parabacteroides, Dialister, Akkermansia, and genera within the family Lachnospiraceae (e.g., not Lachnospira). For example, one embodiment of the edible compositions described herein includes a population of Parabacteroides. Another embodiment of the edible compositions described herein includes a population of Dialister. Another embodiment of the edible compositions described herein includes a population of Akkermansia. Another embodiment of the edible compositions described herein includes a population of Lachnospiraceae. For example, certain embodiments of the edible compositions described herein include populations of Parabacteroides and Dialister; Parabacteroides and Akkermansia; Parabacteroides and Lachnospiraceae; Dialister and Akkermansia; Dialister and Lachnospiraceae; Akkermansia and Lachnospiraceae; Parabacteroides, Dialister, and Akkermansia; Parabacteroides, Dialister, and Lachnospiraceae; Parabacteroides, Akkermansia, and Lachnospiraceae; Dialister, Akkermansia, and Lachnospiraceae; or Parabacteroides, Dialister, Akkermansia, and Lachnospiraceae.

Of course, as the person of ordinary skill in the art will appreciate, the edible compositions including specific combinations of bacteria populations as described herein can further include other bacteria populations, either as elsewhere described herein or otherwise. For example, the compositions can further include one or more bacteria populations selected from the genera Bifidobacterium and Lactobacillus.

The edible compositions can, for example, be provided as food compositions as described below. In other embodiments, an edible composition is provided as a nutritional supplement. In still other embodiments, an edible composition is provided as an ingredient to be mixed with a food composition, for example, during processing or cooking, or at the time of serving or eating. The edible compositions can, for example, be provided with the fermentable soluble fiber, e.g., soluble corn fiber, concentrations, the serving sizes and/or the amounts of fermentable soluble fiber, e.g., soluble corn fiber, per serving as described herein. The amount of the bacterial populations added to the composition may be adjusted by the person of skill in the art to meet the desired need. In general, each of the bacterial populations may be in the amount of about $1 \times 10^3$ to about $1 \times 10^{10}$ CFU (colony-forming unit). In certain embodiments, each of the bacterial populations is in the amount of about $1 \times 10^5$ to about $1 \times 10^{10}$ CFU, or about $1 \times 10^6$ to about $1 \times 10^{10}$ CFU, or about $1 \times 10^7$ to about $1 \times 10^{10}$ CFU, or about $1 \times 10^8$ to about $1 \times 10^{10}$ CFU, or about $1 \times 10^3$ to about $1 \times 10^8$ CFU, or about $1 \times 10^4$ to about $1 \times 10^8$ CFU, or about $1 \times 10^5$ to about $1 \times 10^8$ CFU, or about $1 \times 10^6$ to about $1 \times 10^8$ CFU, or about $1 \times 10^5$ to about $1 \times 10^7$ CFU, or about $1 \times 10^4$ CFU, or about $1 \times 10^5$ CFU, or about $1 \times 10^6$ CFU, or about $1 \times 10^7$ CFU or about $1 \times 10^8$ CFU, or about $1 \times 10^9$ CFU, or about $1 \times 10^{10}$ CFU.

Another embodiment of the invention is an edible composition as described above that further includes one or more mineral species. Each mineral species can, for example, be a divalent mineral species, or a species selected from a calcium species, a magnesium species, a copper species, a potassium species, a zinc species and an iron species. For example, in one embodiment, the edible composition includes calcium. In another embodiment, the edible composition includes calcium and/or magnesium. In another embodiment, the edible composition includes calcium, magnesium, and/or iron. The mineral species can be provided, for example, as a salt, such as a carbonate salt, a halide salt, or a bicarbonate salt. Calcium, for example, can be provided as, e.g., calcium carbonate or calcium gluconate. The mineral (e.g., the calcium) can be provided, for example, at an amount of at least about 50 mg per dose or serving, at least about 100 mg per dose or serving, at least about 250 mg per dose or serving, at least about 500 mg per dose or serving, or even at least about 1000 mg per dose or serving. In certain such embodiments, the calcium is included at less than about 2000 mg per dose or serving or even less than about 1000 mg per dose or serving. The edible compositions can, for example, be provided as food compositions as described below. In other embodiments, an edible composition is provided as a nutritional supplement. The edible compositions can, for example, be provided with the fermentable soluble fiber, e.g., soluble corn fiber, concentrations, the serving sizes and/or the amounts of fermentable soluble fiber, e.g., soluble corn fiber, per serving as described herein.

In other embodiments, the composition of the disclosure does not include a mineral species as described above.

Another embodiment of the invention is an edible composition as described above that further includes one or more additional prebiotics. Examples of prebiotics include, but are not limited to, inulin, lactulose, fructooligosaccharide, mannooligosaccharide, larch arabinogalactan, xylooligosaccharide, polydextrose, and tagatose. In certain embodiments, the disclosure provides edible compositions as described above, wherein the prebiotic is in the range of 0.025 g to 10 g. In certain embodiments, the prebiotic is in the amount of about 0.1 to about 10 g, or about 1 to about 10 g, or about 0.1 to about 5 g, or about 1 to about 5 g, or about 5 to about 10 g, or about 5 to about 8 g, or about 2 to about 8 g, or about 2 to about 5 g, or about 2 to about 8 g, or about 0.05 g, or about 0.1 g, or about 1 g, or about 2 g or about 5 g, or about 8 g, or about 10 g.

In one embodiment, the composition of the disclosure does not include one or more additional prebiotics as described above. For example, in one embodiment, the compositions of the disclosure do not include one or more of the prebiotics selected from the group consisting of inulin, lactulose, fructooligosaccharide, mannooligosaccharide, larch arabinogalactan, xylooligosaccharide, polydextrose, and tagatose. In another embodiment, the compositions of the disclosure does not include inulin. In yet another embodiment, the compositions of the disclosure does not include pullulan.

Optionally, an edible composition or a food composition can also include additional nutritive or non-nutritive saccharides and/or polysaccharides. In one embodiment, the edible composition comprises sorbitol, pullulan, or a combination thereof. Sorbitol delivers about 60% of the sweetness of sugar to foods, but at a significant reduction in caloric content (2.6 vs. 4.0 kcal/g, Livesay) and with a negligible glycemic response. Pullulan gum is a slowly digestible carbohydrate that gives about a 50% relative glycemic response in humans compared to rapidly digestible carbohydrate, but may deliver similar caloric content as sugar to foods.

In one embodiment, the food product comprises about 50-99% fermentable soluble fiber, e.g., soluble corn fiber, 0-50% fructose, 0-33% pullulan, and 0-33% sorbitol, provided that the concentration of at least one of fructose, pullulan, or sorbitol is at least 1%. (All of these percentages are by weight.) In another embodiment, the food product comprises about 60-80% fermentable soluble fiber, e.g., soluble corn fiber, 1-20% fructose, 0-20% pullulan, and 0-20% sorbitol. In yet another embodiment, the food product comprises about 65-75% fermentable soluble fiber, e.g., soluble corn fiber, 5-15% fructose, 5-15% pullulan, and 5-15% sorbitol. In embodiments that comprise a high intensity sweetener, the concentration of that ingredient can be about 0.001-0.5%.

The edible composition or food composition optionally can also contain resistant starch or other fiber sources.

As the person of skill in the art will appreciate, the compositions described herein can be used in practicing the methods described elsewhere herein.

The terms "edible" and "edible composition" are used in a broad sense herein to include a variety of substances that can be ingested by humans, such as food, beverages and medicinal and nutritional supplement dosage forms such as syrups, powders, capsules or tablets. The terms "food" and "food composition" are used more narrowly to mean foods and beverages and ingredients therefor. Suitable food compositions can be in a variety of forms including, but are not limited to baked foods, breakfast cereal, dairy products, soy products, confections, jams and jellies, beverages (powdered and/or liquid), shakes, fillings, yogurts (dairy and non-dairy yogurts), kefirs, extruded and sheeted snacks, gelatin desserts, snack bars, meal replacement and energy bars, cheese and cheese sauces (dairy and non-dairy cheeses), edible and water-soluble films, soups, syrups, table top sweeteners, nutritional supplements, sauces, dressings, creamers, icings, ice cream, frostings, glazes, pet food, tortillas, meat and fish, dried fruit, infant and toddler food, and batters and breadings.

In order to make the food product suitable for use as a flavor enhancer in food compositions, in many cases it will be desirable for it also to include a natural and artificial flavors. Suitable examples of such flavors include apple, citrus, grape, orange, cherry, lemon, lime, vanilla, peach, peanut butter, pineapple, pomegranate, blueberry, raspberry, blackberry, jasmine, lavender, mint, strawberry, banana, mango, passion fruit, dragon fruit, kiwi, chocolate, maple, rum, butter, and combinations thereof.

In certain embodiments, the edible composition is in the form of an agglomerated powder, for example, like those used in making powdered drinks and nutritional supplements.

In order to make the food product suitable for use as a sweetener composition in food, in many cases it will be desirable for it also to include a non-nutritive high-intensity sweetener. Suitable examples of such non-nutritive high-intensity sweeteners include, but are not limited to sucralose, acesulfame potassium, aspartame, monkfruit, Stevia, and combinations thereof.

The person of ordinary skill in the art will appreciate that the fermentable soluble fiber, e.g., soluble corn fiber, can be provided in any of several different physical forms, such as powder, agglomerated powder, syrup or concentrated syrup solids. In one embodiment, the soluble fiber is in particulate form. The particulates can be held together by a binder, such as a binder composition that comprises a major amount of maltodextrin. An agglomeration of particulates can have advantages in terms of rate of dissolution and dispersion. This can be useful in applications where more rapid dissolution and lower shear rates of mixing are important, such as table top sugar replacement, table top fiber supplementation, and on-the-go dry powder drink mix products.

Additional aspects suitable for use in edible compositions as described herein are described further in U.S. Patent Applications Publications nos. 2008/0292766, 2006/0210696 and 2008/0175977, each of which is hereby incorporated herein by reference in its entirety, and which is attached in the appendix to this specification. In certain embodiments of the methods and compositions described herein, the edible composition is in a form and uses additional ingredients as described in an aspect or embodiment of U.S. Patent Application Publication no. 2008/0292766, 2006/0210696 or 2008/0175977.

Certain aspects of the invention are further described with respect to the experimental studies described below.

Example 1

Subjects and Methods
Subjects

Fifteen boys, aged 13-15 y, and 9 girls, aged 12-14 y, participated in these metabolic studies. Screening questionnaires were used to determine eligibility based on a brief medical history, maturational age, physical activity, and habitual dietary intake assessed with a 6-day diet record. Exclusion criteria included abnormal liver or kidney function, malabsorptive disorders, anemia, smoking, history of medications that influence calcium metabolism (steroids, thiazide diuretics), body weight outside the 5-95$^{th}$ BMI percentile for age, regular consumption of illegal drugs, non-prescription drugs, or any kind of contraceptives, and pregnancy. Subjects were not permitted to take nutritional supplements while participating in these studies and were asked to discontinue use before coming to camp.

Study Design

This study, designed to have a summer camp environment, was composed of two 3-week balance studies separated by a 7-day washout period. This trial used a double-blind, cross-over design in which participants received two treatments in randomized order, 12 g soluble corn fiber or placebo.

Diets

Controlled diets were provided throughout both camp sessions and contained foods that are typically eaten by adolescent children such as spaghetti, hamburgers, sandwiches and potato chips. Subjects were assigned to one of five energy levels (1750, 2100, 2400, 2700, and 3000 kilocalories) based on estimated energy requirements calculated using the Harris-Benedict equations. Diets were designed to maintain body weight and to contain constant levels of key nutrients. The controlled diet was provided as a 4-day cycle menu with 3 meals and 2 snacks daily. On average the diet contained 14% protein, 33% fat, 53% carbohydrate, 200 IU vitamin D, 1100 mg phosphorus, 2300 mg sodium, and 600 mg calcium. Fifteen grams of fiber was included in the basal diet and the intervention added an additional 0 or 12 g of SCF. This yielded a total dietary fiber content of 15 and 27 g for the Control and SCF treatments, respectively. SCF was given in WELCH'S® fruit snacks and divided into two 0 or 6 g doses provided at lunch and dinner. SCF provided by Tate & Lyle Health & Nutrition Sciences (Hoffman Estates, Ill.), contained >70% soluble dietary fiber with an approximate weight-average degree of polymerization of 10 and $\alpha$-1,4, $\alpha$-1,6, $\alpha$-1,3, and $\alpha$-1,2 bonds.

Anthropometrics and Bone Measurements

Anthropometric measures including weight, sitting height, bitrochanteric width, waist circumference, and hip circumference were taken during the first session of camp. Standing height using a wall-mounted stadiometer was measured at the beginning of the first session and weight was monitored in the morning on each day with an electronic digital scale to ensure that weight remained stable throughout the sessions. Bone mineral content (BMC) and bone mineral density (BMD) were measured by dual energy x-ray absorptiometry (DXA) (GE Lunar, Madison, Wis.) during one balance period. Bone measurements were taken of the total body, spine, forearm, and both hips.

Hormones and Biochemical Markers of Bone Metabolism

A fasting, baseline blood draw was taken on the first day of camp for determination of general blood chemistries to verify clinical profiles and health of the participants. A second fasting sample was taken at the end of camp to measure biochemical markers of bone dynamics and hormones related to calcium and vitamin D metabolism.

Sample Collection and Analysis

All urine and fecal samples were collected from day 1 to 21 of each balance period and pooled as 24-h collections. Calcium content of diet, fecal, and urine samples was measured using inductively coupled plasma optical emission spectrometry (Optima 4300 DV, Perkin Elmer Instrument) as previously described. All fecal samples were frozen and processed at a later time for calcium. Urine was refrigerated and also analyzed later for total calcium content.

Compliance

Participants were supervised during activities, meals, and sample collection by trained counselors for 24 h each day. Unconsumed food from meals was collected and recorded. Urine collection compliance was evaluated by measuring creatinine excreted in urine by enzymatic colorimetric assay (COBAS Integra, Roche Diagnostics). Fecal collection compliance was assessed by polyethylene glycol (PEG) recovery in the feces. Each participant was given 3 g polyethylene glycol (PEG) (E3350; Dow Chemical Co., Midland, Mich.) divided into 1 g doses at breakfast, lunch and dinner. Percent PEG recovery was measured in 24-h fecal collections by turbidimetric assay and was used as a basis to exclude subject data in the case of poor compliance.

Gastrointestinal Symptoms

The presence of stomach noises, flatulence, bloating and abdominal pain among subjects was evaluated daily using a short questionnaire. The severity of gastrointestinal symptoms were assessed daily by self-report using a scale of 1-10 (0=none, 10=very severe) for 18 days during the second camp session.

Fractional Calcium Absorption Test

During the last week of each session, following an overnight fast, the subjects participated in a calcium absorption test. On the morning of the test, phlebotomists inserted catheters and drew 10 ml baseline venous samples Immediately after the blood draw, participants consumed a breakfast consisting of an English muffin, scrambled eggs, butter and jam. The meal contained 150 mg calcium (Ca) from 2% milk plus 15 mg $^{44}$Ca, a stable non-radioactive isotope. The oral isotope was administered as a liquid (CaCl$_2$) which was added to the milk and allowed to equilibrate overnight. Following breakfast, participants were not allowed to consume any food but were allowed to drink ad libitum deionized water. A second stable isotope, $^{43}$Ca (3.5 mg) also as calcium chloride, was given intravenously one hour after the consumption of breakfast and the oral isotope. A final blood draw was performed three hours after administration of the intravenous dose after which catheters were removed and subjects were served lunch.

Absorption and Retention Calculations

Two 24-h urine pools were used to measure changes in fractional calcium absorption over 48 hours following calcium isotope administration. Urine samples collected in 24-h pools for two days (0-24 h and 24-48 h) after the absorption test were analyzed for $^{44}$Ca and $^{43}$Ca enrichment by high resolution inductively coupled plasma mass spectrometry (ICP-MS, Finnegan Element2, Thermo Scientific). Calcium absorption (Equation 1) was calculated using enrichment values to calculate the Δ excess for $^{44}$Ca and $^{43}$Ca as the difference of 0-24 h and 24-48 h samples from baseline, divided by baseline. These excess values were then expressed as a ratio of $^{44}$Ca/$^{43}$Ca based on their natural abundances and multiplied by the quantity of the iv dose (mg) divided by the oral dose (mg).

Fractional Ca Absorption = Equation 1

$$\left[\left[\left(\frac{^{44}Ca\Delta excess}{^{43}Ca\Delta excess}\right) * \left(\frac{0.02083}{0.00135}\right)\right] * \left[\frac{iv\ dose}{oral\ dose}\right]\right]$$

Balance data were used to calculate calcium retention (Equation 2) by subtracting 24-h calcium excretion in urine and feces from 24-h dietary calcium intake. The first 7 days of each 3-week study were regarded as an equilibration period for participants to acclimate to calcium intake and the fiber treatment, while the remaining 2 weeks acted as the experimental period. Balance was calculated based on as many of the 14 days in the experimental portion as possible, so long as it allowed calculations to begin and end on days with fecal samples. Periods between stools were divided by the appropriate number of days. Daily urinary calcium excretion values used in balance calculations were corrected for variation in timing of collections and incomplete collections by adjusting 24 h urinary calcium for daily creatinine excretion (Equation 3). Calcium retention was calculated using both uncorrected and corrected values for urinary calcium excretion. Apparent calcium absorption (Equation 4) was determined as the difference between calcium intake and fecal calcium excretion while net calcium absorption efficiency (Equation 5) was calculated as intake minus fecal excretion, divided by intake.

Calcium Retention = Dietary Ca Intake-Urinary Ca-Fecal Ca      Equation 2

Corrected 24 h Urine Ca Excretion =      Equation 3

$$\frac{24\ h\ Urinary\ Ca\ (mg)}{\left[\frac{24\ h\ Creatinine\ (mg)/Avg\ 24\ h\ Creatinine}{Excretion\ for\ Balance\ Period\ (mg)}\right]}$$

Apparent Ca Absorption =      Equation 4
Dietary Ca Intake-Fecal Ca Excretion

Net Ca Absorption Efficiency =      Equation 5

$$\frac{Dietary\ Ca\ Intake\ (mg) - Fecal\ Ca\ (mg)}{Dietary\ Ca\ Intake} * 100$$

Statistical Analysis

Statistical analyses were performed using SAS (version 9.2; SAS Institute, Cary, N.C.). Baseline characteristics of females and males were compared using t-tests. Wilcoxon's rank-sum test was used to assess differences in nonparametric gastrointestinal symptoms. Pearson's correlations were used to examine potential associations between the change in fractional Ca absorption in 24-48 h urine (absorption on SCF minus absorption on control) and the differences in calcium balance and vitamin D status, baseline anthropometrics, and measures of bone density and strength. A general linear model was used to assess the effect of SCF on fractional calcium absorption. The model accounted for the crossover design by nesting id within sequence as a random effect variable and controlled for phase (first versus second 3-week camp session) and sequence of treatments. The data were analyzed separately for each time period (0-24 h and 24-48 h). Similar analyses were performed for calcium balance. Using published means and standard deviations for fractional calcium absorption reported in adolescent children, it was determined that a sample size of 24 would provide sufficient power (80%) to see a 5.9% difference in calcium absorption assuming an alpha error of 0.05 and a standard deviation of 2.9±9.6%. P-values<0.05 were considered statistically significant for all statistical tests.

Results

A total of 24 subjects (9 girls and 15 boys) participated in this study. Three subjects did not participate in the fractional calcium absorption test in both sessions. Therefore, fractional calcium absorption was analyzed for 21 subjects. All other analyses included all available data values. The participants evaluated in this study were ethnically diverse with a distribution of 11 Asian, 6 Hispanic, 1 Black, and 6 multi-racial teens (Other). Subject characteristics including age, anthropometrics, physical characteristics, and bone measures are given in Table 1 which presents means and standard deviations for girls and boys separately. Girls and boys had similar physical characteristics; there were statistically significant differences only in % lean (girls lower than boys, P=0.009) and % fat mass (girls higher than boys, P=0.01) in this cohort. Mean habitual intakes of calcium and dietary fiber were 768±403 mg/d and 12±4 g/d, respectively.

TABLE 1

Baseline subject characteristics

| | Females (n = 9) | Males (n = 15) |
|---|---|---|
| Age (y) | 13.3 ± 1.0 | 13.5 ± 0.9 |
| Weight (kg) | 59.9 ± 13.2 | 61.1 ± 11.8 |
| Height (cm) * | 157.3 ± 4.9 | 164.9 ± 8.2 |
| BMI (kg/m$^2$) | 24.1 ± 4.0 | 22.4 ± 3.1 |
| BMI Percentile (%) | 80.0 ± 16.4 | 74.7 ± 19.2 |
| Tanner Score Average ** | 3.8 ± 0.7 | 2.4 ± 0.9 |
| Lean mass (%) ** | 61.2 ± 5.2 | 71.1 ± 9.5 |
| Fat mass (%) * | 35.1 ± 5.6 | 25.1 ± 10.0 |
| Total Body BMD (g/cm$^2$) | 1.07 ± 0.11 | 1.04 ± 0.11 |
| Total Body BMC (g) | 2115 ± 329 | 2316 ± 424 |
| Total Spine BMD (g/cm$^2$) | 1.09 ± 0.13 | 1.04 ± 0.14 |
| Femoral Neck BMD (g/cm$^2$) | 1.03 ± 0.18 | 1.05 ± 0.15 | t-test; Mean ± SD
* Significant difference between boys and girls (p < 0.05)
** Significant difference between boys and girls (p < 0.01)

Gastrointestinal Symptoms

No significant differences in the severity of gastrointestinal symptoms, including bloating, flatulence, abdominal cramping, and stomach noises were seen between SCF and Control treatments over the 18 day observation period (Table 2).

TABLE 2

Self-reported mean daily gastrointestinal symptoms over 18 days in response to SCF consumption.

| | Soluble Corn Fiber | Control |
|---|---|---|
| Bloating | 0.1 ± 0.3 | 0.3 ± 0.8 |
| Flatulence | 0.6 ± 0.8 | 1.1 ± 1.7 |
| Abdominal Cramping | 0.3 ± 0.5 | 0.4 ± 0.7 |
| Stomach Noises | 0.2 ± 0.7 | 0.3 ± 0.9 |

Wilcoxon's rank-sum test; Mean ± SD
N = 23
P > 0.05 for all parameters
Scores were assigned based on a 10 point scale: 0 = none, 1 = very mild, and 10 = very severe.

Fractional Calcium Absorption, Calcium Balance and Bone Biomarkers

Figure 2:
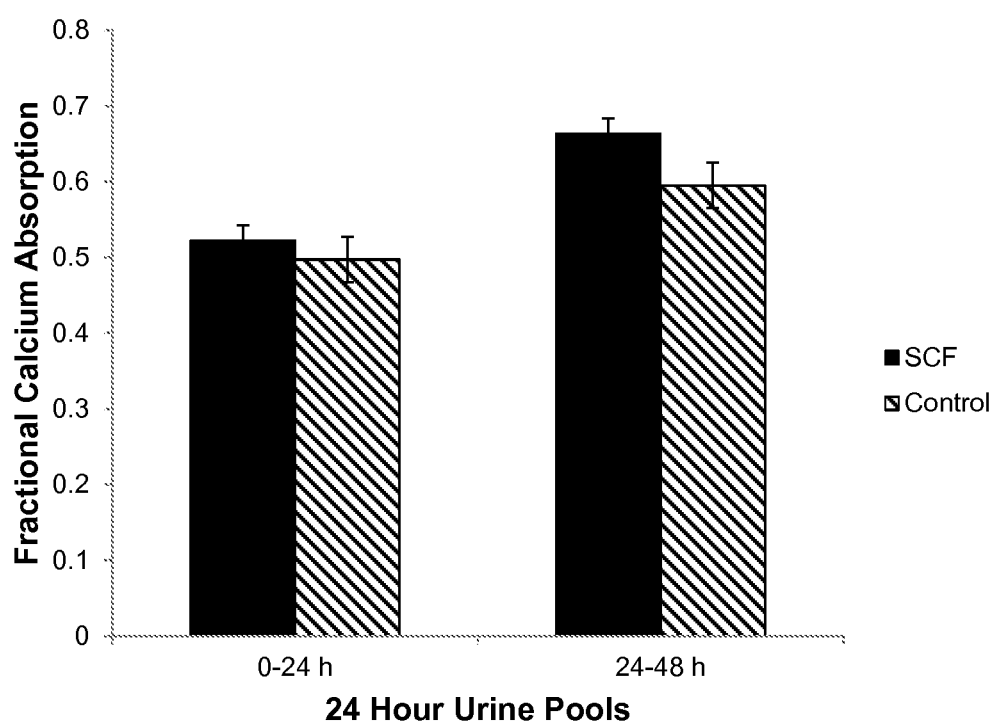
FIG. 2 shows comparison of SCF and Control treatments on fractional calcium absorption measured by 0-24 h and 24-48 h urine collections.

Fractional calcium absorption was based on analysis of isotopes excreted in urine collected between 0-24 and 24-48 hours after isotope administration (FIG. 1). Compared with the control, mean fractional calcium absorption did not differ during the first 24 h but was significantly higher after treatment with SCF (0.595±0.142 vs. 0.664±0.129, respectively; P=0.02) at 24-48 h. The difference in mean fractional calcium absorption of 0.069 represents an 11.6% increase in absorption with SCF treatment. A general linear model (FIG. 2) identified significant effects of treatment at 24-48 h (P=0.02) but not at 0-24 h (P=0.09) on fractional calcium absorption. Treatment had no significant effect on net calcium absorption, net absorption efficiency, fecal calcium excretion or calcium retention (Table 3). Neither urine nor fecal calcium excretion were correlated with fractional calcium absorption. Bone turnover marker concentrations are reported in Table 4. No differences in serum alkaline phosphatase, phosphorus, calcium, parathyroid hormone, leptin, insulin-like growth factor (IGF)-1, IGF-binding protein-3, sclerostin, and urine n-telopeptide cross links, calcium and phosphorus resulted from SCF consumption.

TABLE 3

Effect of soluble corn fiber treatment on calcium absorption and retention in 23 adolescent boys and girls

|  | SCF | Control | P-value |
| --- | --- | --- | --- |
| Stable Isotope Analysis | | | |
| Fractional Calcium Absorption, 0-24 h | 0.522 ± 0.110 | 0.497 ± 0.108 | 0.09 |
| Fractional Calcium Absorption, 24-48 h | 0.664 ± 0.129 | 0.595 ± 0.142 | 0.02 |
| Balance | | | |
| Calcium Intake (mg/d) | 606 ± 29 | 604 ± 25 | 0.69 |
| Urine Calcium (mg/d) | 77 ± 56 | 65 ± 36 | 0.11 |
| Fecal Calcium (mg/d) | 318 ± 108 | 312 ± 106 | 0.77 |
| Net Absorption Efficiency (%) | 47 ± 18 | 48 ± 17 | 0.75 |
| Retention (mg/d) | 212 ± 117 | 227 ± 101 | 0.42 |

General linear model that includes treatment, sequence, and phase
Mean ± SD
N = 21 for fractional calcium absorption values

TABLE 4

Serum and urine bone turnover marker concentrations at baseline and after treatment with 0 and 12 g SCF

| Bone Biomarker | SCF | Control | P-value |
| --- | --- | --- | --- |
| Serum | | | |
| Alkaline Phosphatase, U/L | 235.57 ± 135.45 | 235.00 ± 132.5 | 0.92 |
| Calcium, ng/dl | 10.23 ± 0.40 | 10.24 ± 0.40 | 0.72 |
| Creatinine, ng/dl | 0.85 ± 0.12 | 0.85 ± 0.12 | 0.88 |
| Phosphorus, ng/dl | 4.76 ± 0.59 | 4.76 ± 0.58 | 0.21 |
| Parathyroid Hormone, pg/ml | 21.23 ± 11.27 | 21.23 ± 11.02 | 0.82 |
| Leptin, ng/ml | 8.65 ± 7.61 | 8.46 ± 7.50 | 0.89 |
| IGF-1, | 266.81 ± 52.30 | 269.59 ± 52.93 | 0.87 |
| IGF- Binding Protein 3 | 3648.99 ± 572.71 | 3651.26 ± 560.23 | 0.46 |
| Sclerostin, ng/ml | 0.41 ± 0.17 | 0.41 ± 0.17 | 0.47 |
| Urine | | | |
| N-telopeptide Crosslinks, nm BCE | 5378.81 ± 4632.47 | 5323.75 ± 4538.67 | 0.63 |
| Calcium, mg/dl | 3.43 ± 2.51 | 3.37 ± 2.47 | 0.69 |
| Phosphorus, mg/dl | 77.85 ± 39.97 | 76.69 ± 39.51 | 0.66 |
| Creatinine, mg/dl | 90.297 ± 45.721 | 90.67 ± 44.75 | 0.56 |

Mean ± SD

Vitamin D Status and Calcium Absorption

Mean vitamin D status after SCF and Control treatments was 65.2±18.8 nM and 59.1±15.9 nM, respectively, which were not significantly different. No significant associations between differences in 25-hydroxyvitamin D and fractional calcium absorption (between 24-48 h) or net absorption efficiency were observed.

Predictors of the Effect of SCF on Calcium Absorption

The difference in fractional calcium absorption between SCF and Control treatments in 24-48 h urine collections was not correlated with height (r=0.112, P=0.63), body surface area (r=0.012, P=0.96), weight (r=−0.022, P=0.92), habitual dietary fiber (r=0.150, P=0.54) and calcium (r=0.012, P=0.96) intakes, Tanner stage (r=−0.131, P=0.57), or BMI (r=−0.074, P=0.75).

Example 2

Fecal Processing and DNA Extraction

Microbial community composition and structure in feces was determined in samples collected at the beginning and end of each session for each subject of Example 1. Frozen fecal samples were weighed, thawed at 4° C., then sterilized double distilled water (twice the weight of the fecal samples) was added and samples were homogenized in a stomacher. Fecal slurries were stored at −20° C. until DNA was extracted. DNA was extracted from 50-100 mg of fecal material using the FastDNA® SPIN kit for Soil (MP Biochemicals, Irvine, Calif.). DNA quality was checked using a 0.7% agarose gel and Nanodrop 1000 spectrophotometer (Thermo Scientific, Wilmington, Del.) and then quantified using a Nanodrop 3300 fluorospectrometer (Thermo Scientific).

Microbial Community Composition Using Pyrosequencing

The phylogenetic diversity of bacterial communities was determined using 16S rRNA gene sequences obtained using 454 FLX titanium chemistry and Roche Genome Sequencer (454 Life Sciences-Roche, Branford, Conn.) and primers that amplify the V3-V5 region of the 16S rRNA gene. Multiple samples were run and differentiated using 10-bp tagged forward primers. Initial PCR from fecal samples extracts was performed using high fidelity Phusion DNA Polymerase (NEB) and amplicons were gel purified (QIAEX II Gel Extraction Kit, Qiagen). At the Purdue Genomics facilities purified amplicons were quantified by fluorometry after staining using the PicoGreen DNA Assay Kit and by qPCR, and equimolar amounts were used for 454 FLX titanium chemistry sequencing.

Statistical Analysis

The reads from pyrosequencing analysis were first pre-processed using software to remove primer tags and to remove low quality sequences. Sequence quality was considered low if the length was <400 bp or if there were mismatches or ambiguities in the forward primer sequence. Sequences were analyzed using the QIIME pipeline that includes software from many sources that allows Operational Taxonomic Unit (OTU) and taxonomic assignment as well as a number of different beta and alpha diversity measures. Chimerslayer was used to remove chimeric sequences. The OTU assignments were made using the uclust method and furthest neighbor clustering with a 97% sequence similarity threshold. Representative OTU sequences were obtained after sequence alignment using PyNast and the Greengenes core set. Taxonomic assignments were made using the RDP classifier at 80% confidence. Rarefaction analysis was used to obtain an estimation of sequence coverage of the community. Alpha biodiversity estimations (e.g., Shannon and Chao1 indices) were calculated to compare subjects, with the caveat that PCR is being used to target the 16S rRNA gene results might have been biased and differences in sequence copy per genome would influence relative numbers. Community composition comparisons were made using "Fast UniFrac" analysis of both OTU and phylogenetic datasets.

Pearson's correlation analysis was used to look for associations between the difference in fractional calcium absorption between treatments (24-48 h) and the difference in the presence of bacteria genera after each treatment. Bacteria used in these correlations were for bacteria with genera average≥0.001 (=0.1%) or taxa proportions that were significantly different in end samples based on t-tests which included the following bacterial taxa: *Bifidobacterium*, Other Coriobacteriaceae, *Bacteroides, Barnesiella, Butyricimonas, Parabacteroides, Prevotella, Alistipes*, Other Rikenellaceae, *Enterococcus, Lactobacillus*, Other Lactobacillaceae, Streptococcus, *Clostridium, Eubacterium, Mogibacterium, Blautia, Anaerostipes, Coprococcus, Dorea*, Other Lachnospiraceae, *Roseburia*, Other Clostridiales, Other Peptostreptococcaceae, *Sporacetigenium, Acetivibrio, Butyricicoccus, Faecalibacterium, Oscillibacter*, Other Ruminococcaceae, *Ruminococcus, Subdoligranulum, Dialister*, Other *Clostridia, Catenibacterium, Coprobacillus*, Other Erysipelotrichaceae, *Turicibacter*, Other Firmicutes, Other Bacteria, *Escherichia/Shigella, Pseudomonas, Actinomyces*, Other Streptococcaceae, *Anaerofustis*, and *Anaerococcus*.

Results
Changes in Bacterial Community Composition

A total of 1,793,821 sequences were obtained using 454-Titanium pyrosequencing (Roche Applied Science, Branford, Conn., USA) with an average of 19498 sequences (±7126) per sample, and a range between 8211 and 41212 sequences per sample. There were no significant differences in the number of sequences obtained for each subject when compared by either treatment (P>0.05) or by time of collection (baseline vs. end samples) (P>0.05). There were ten phyla, Actinobacteria, Bacteroidetes, Firmicutes, *Proteobacteria*, Cyanobacteria, Fusobacteria, TM7, Verrucomicrobia, Spirochaetes and Synergistetes represented in the microbial communities of the 23 subjects. But in all samples more than 99% of the sequences were from four phyla; Firmicutes was the most dominant phylum with an average of 89.4% followed by Bacteroidetes (5.1%), Actinobacteria (4.9%) and *Proteobacteria* (0.5%).

Figure 3:
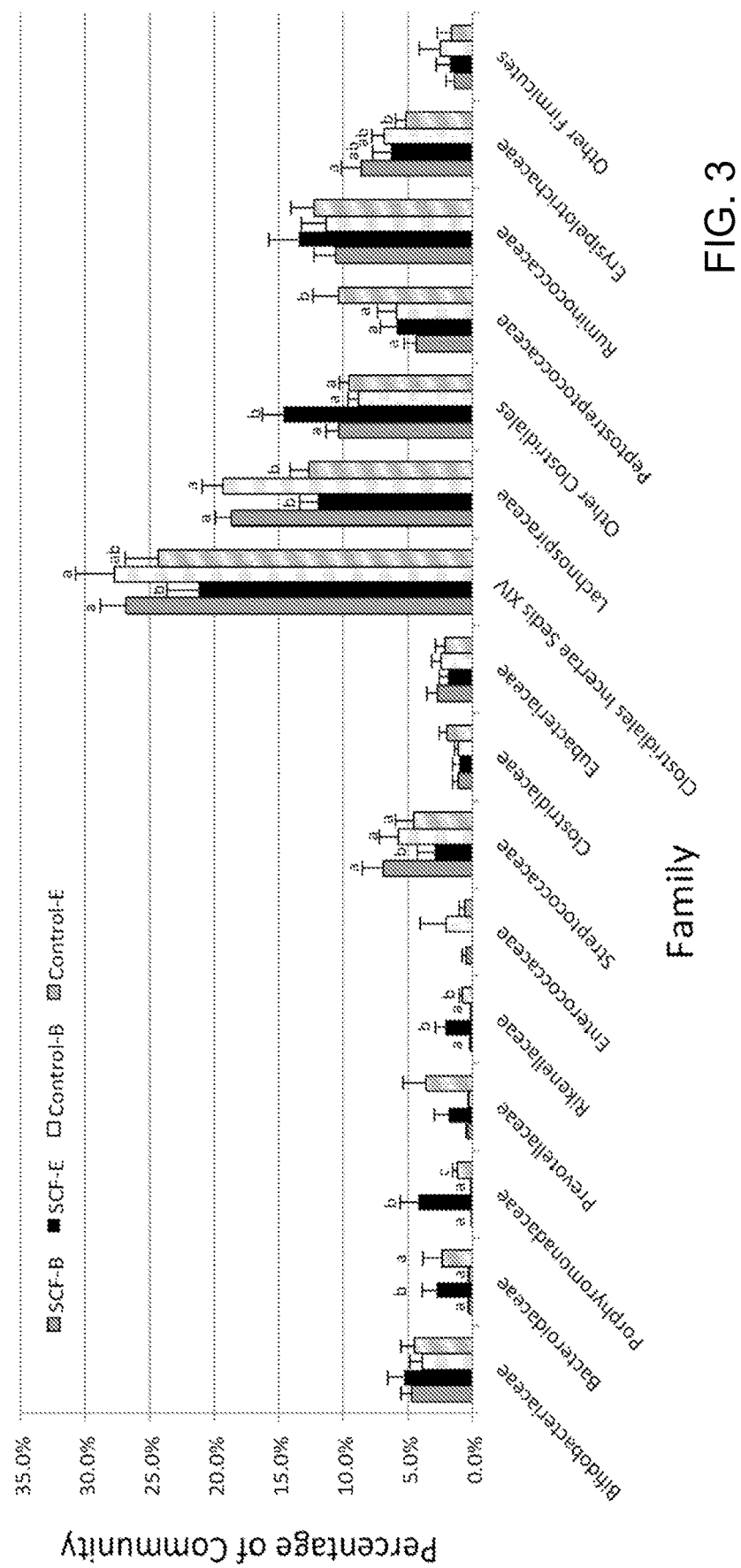
FIG. 3 shows a comparison of average relative proportions of bacterial families in subjects at the beginning (B) and end (E) of clinical sessions where diets included soluble corn fiber (SCF) vs control (Con). Only families representing >1.0% of the total community in at least one treatment are depicted. Error bars represent standard errors of means. Letters depict significant differences within each family (p<0.05).
Figure 4:
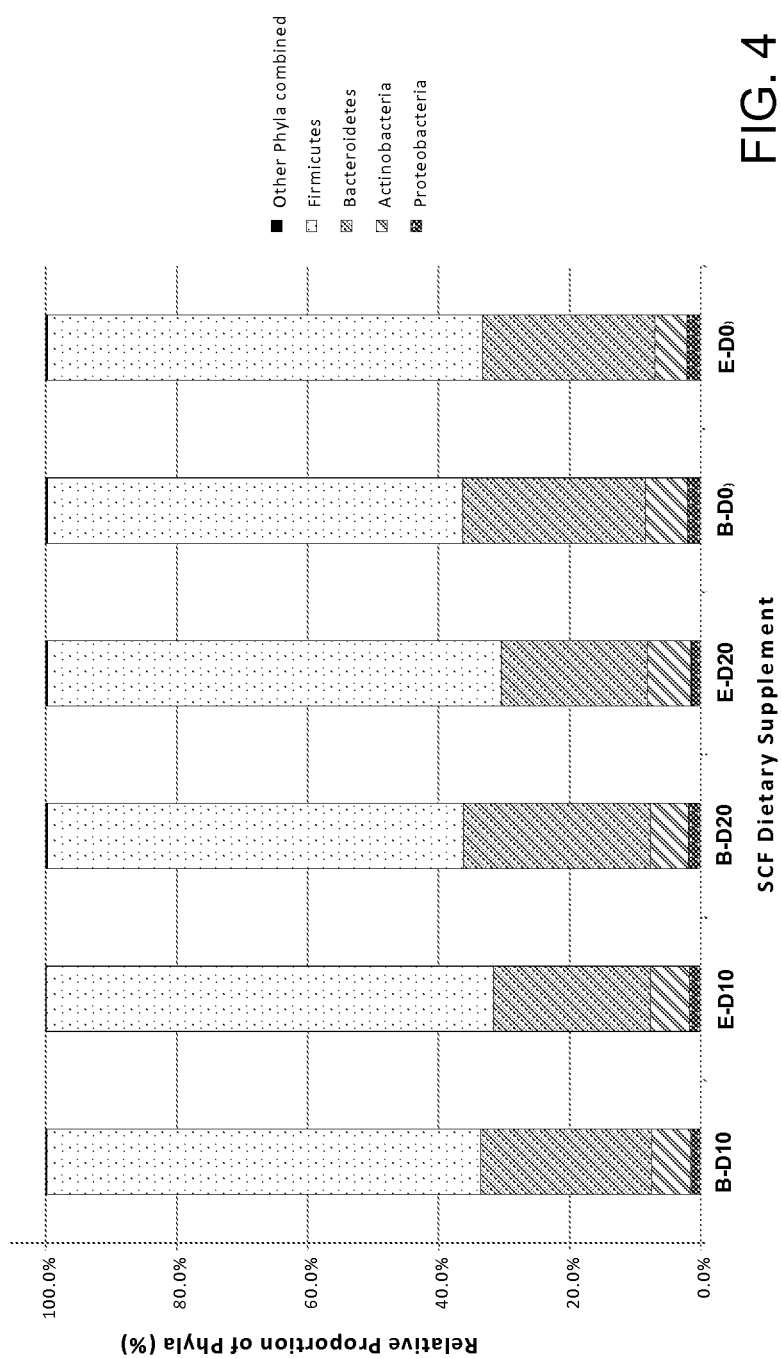
FIG. 4 shows a histogram comparing average proportion of major bacterial phyla at the beginning (B) and end (E) of each SCF diet treatment.

At the phylum level, regardless of the inclusion of SCF in the clinical diet, the average relative proportion of Bacteroidetes significantly increased and Firmicutes decreased by the end of each session. Communities from subjects on SCF versus Control treatments were significantly different at the family level (FIG. 3). There was a higher proportion of Porphyromonadaceae (P=0.02) and other Clostridiales (P=0.009) after the SCF diet and lower Peptostreptococcaceae (P=0.04). There was a significant difference in relative population proportions in the family Corynebactariaceae (P=0.02) at the beginning of the two treatments. At the lowest level of resolution for these sequences there were nine genera and four "other" groups that had average proportions that differed significantly (P<0.1) after the SCF versus Control treatments (Table 5). The significant increases after the SCF diet were in the genera *Parabacteroides* (P<0.003), other Clostridiales (P=0.04) and other Ruminococcaceae (P<0.03) while significant decreases were observed for *Enterococcus* (P<0.03), *Anaerofustis* (P<0.05), *Coprococcus* (P<0.03) and other Peptostreptococcaceae (P<0.002). There was also an increase in *Bifidobacterium, Alistipes, Anaerococcus, Catenibacterium* and other *Clostridia* but the increases were not significant. Similarly, decreases in *Rothia*, other *Streptococcaceae, Clostridium, Sporacetigenium, Turicibacter* and other TM7 genera incertae sedis occurred with SCF consumption but the difference in community proportion with CON was not significant.

TABLE 5

Comparison of average (±SEM) proportion of bacterial taxa in subject fecal samples at end of soluble corn fiber supplemented versus control diets

| Taxon* | SCF | CON | P-value |
|---|---|---|---|
| Phylum: Actinobacteria | | | |
| Class: Actinobacteria; Order: Actinomycetales; Family: Micrococcaceae | | | |
| Genus: *Rothia* | 0.001 ± 0.002% | 0.016 ± 0.061% | 0.065 |
| Class: Actinobacteria; Order: Bifidobacteriales; Family: Bifidobacteriaceae | | | |
| Genus: *Bifidobacterium* | 5.26 ± 1.18% | 4.38 ± 1.03% | 0.095 |
| Phylum: Bacteroidetes | | | |
| Class: Bacteroidia; Order: Bacteroidales; Family: Porphyromonadaceae | | | |
| Genus: *Parabacteroides* | 3.58 ± 1.18% | 0.83 ± 0.32% | 0.003 |
| Class: Bacteroidia; Order: Bacteroidales; Family: Rikenellaceae | | | |
| Genus: *Alistipes* | 1.77 ± 0.62% | 0.57 ± 0.19% | 0.060 |
| Class: Other Bacteroidetes | 0.01 ± 0.005% | 0.037 ± 0.145% | 0.063 |
| Phylum: Firmicutes | | | |
| Class: Bacilli; Order: Lactobacillales; Family: Enterococcaceae | | | |
| Genus: *Enterococcus* | 0.012 ± 0.037% | 0.590 ± 2.100% | 0.027 |
| Class: Bacilli; Order: Lactobacillales | | | |
| Family: Other Streptococcaceae | 0.001 ± 0.003% | 0.004 ± 0.008% | 0.078 |
| Class: Clostridia; Order: Clostridiales; Family: Clostridiaceae | | | |
| Genus: *Clostridium* | 1.012 ± 2.234% | 1.960 ± 2.778% | 0.077 |

TABLE 5-continued

Comparison of average (±SEM) proportion of bacterial taxa in subject fecal samples at end of soluble corn fiber supplemented versus control diets

| Taxon* | SCF | CON | P-value |
|---|---|---|---|
| Class: Clostridia; Order: Clostridiales; Family: Eubacteriaceae | | | |
| Genus: *Anaerofustis* | 0.006 ± 0.002% | 0.012 ± 0.004% | 0.048 |
| Class: Clostridia; Order: Clostridiales; Family: Incertae Sedis XI | | | |
| Genus: *Anaerococcus* | 0.017 ± 0.007% | 0.003 ± 0.002% | 0.064 |
| Class: Clostridia; Order: Clostridiales; Family: Lachnospiraceae | | | |
| Genus: *Coprococcus* | 0.68 ± 0.13% | 1.15 ± 0.25% | 0.027 |
| Class: Clostridia | | | |
| Order: Other Clostridiales | 14.64 ± 1.63% | 9.61 ± 0.69% | 0.013 |
| Class: Clostridia; Order: Clostridiales; | | | |
| Family: Other Peptostreptococcaceae | 0.42 ± 0.10% | 1.00 ± 0.18% | 0.001 |
| Class: Clostridia; Order: Clostridiales; Family: Peptostreptococcaceae | | | |
| Genus: *Sporacetigenium* | 5.46 ± 1.18% | 9.38 ± 1.92% | 0.083 |
| Class: Clostridia; Order: Clostridiales | | | |
| Family: Other Ruminococcaceae | 4.07 ± 1.02% | 1.93 ± 0.45% | 0.030 |
| Class: Other Clostridia | 0.225 ± 0.413% | 0.124 ± 0.266% | 0.064 |
| Class: Erysipelotrichi; Order: Erysipelotrichales; Family: Erysipelotrichaceae | | | |
| Genus: *Catenibacterium* | 2.297 ± 6.656% | 0.438 ± 1.155% | 0.094 |
| Class: Erysipelotrichi; Order: Erysipelotrichales; Family: Erysipelotrichaceae | | | |
| Genus: *Turicibacter* | 0.308 ± 0.630% | 0.855 ± 1.817% | 0.083 |
| Phylum: TM7 | | | |
| Class: Other TM7_genera_incertae_sedis | 0.001 ± 0.003% | 0.005 ± 0.012% | 0.078 |

*Only taxa in which proportions at the end differed significantly (paired t-test, p-values < 0.1) are listed.

Fast UniFrac with jackknife analysis showed no differences in community structure due to diet despite processing the data using different classification criteria (e.g., OTUs versus phylogeny). Principal coordinate analysis of weighted Unifrac of OTUs showed some separation between samples at the beginning and end of clinical sessions but the two treatments did not separate.

Correlations Between Bacteria Genera and Fractional Calcium Absorption

Changes (SCF treatment minus control) in fractional Ca absorption measured in 24-48 h urine were negatively correlated (decreases in bacterial genera as calcium absorption with SCF increased) with Actinomyces, Pseudomonas from phylum Actinobacteria and other Erysipelotrichaceae from phylum Firmicutes. Conversely, change in fractional Ca absorption was positively correlated (increases in bacterial genera as calcium absorption with SCF increased) with Bacteroidetes member *Bacteroides* as well as *Butyricicoccus, Oscillibacter*, and *Dialister* from the phylum Firmicutes

TABLE 6

Correlations between calcium absorption and bacteria genera that may affect lower gut mechanisms

| Genera differences at | Diff in Ca Abs at 24-48 h | |
|---|---|---|
| end of each treatment | Coefficient | P-value |
| *Bacteroides* | 0.483 | 0.027 |
| *Actinomyces* | −0.553 | 0.009 |
| *Pseudomonas* | −0.473 | 0.03 |
| *Butyricicoccus* | 0.454 | 0.039 |
| *Oscillibacter* | 0.565 | 0.008 |
| *Dialister* | 0.619 | 0.003 |
| Other Erysipelotrichaceae | −0.463 | 0.034 |

Pearson's correlations
N = 21

The above results indicate that daily consumption of 12 g soluble corn fiber for 21 days in adolescent girls and boys increased fractional calcium absorption by ~12%. This increase in fractional calcium absorption occurred between 24 and 48 h as the effect was significant by measuring the second 24-h urine pool (24-48 h) after receiving stable calcium isotopes, while no significant difference was seen in isotope enrichment in urine collected during the first 24-h. This is supported by literature that suggests microbial involvement and lower gut absorption is not captured until 24 h after receiving isotopes.

It is difficult to say whether the increased absorption of calcium seen in this study resulted in bone mineral deposition because no effect was seen on calcium retention. Fecal calcium measures are highly variable; a sample size of 34 would be necessary to see a 61 mg difference in calcium retained with an alpha error of 0.05, 80% power and a standard deviation of the difference between participants of 122 mg/d. It is possible that the treatment elicits an effect on bone strength. The two methods have a large difference in % SD, i.e. 9.7% for breaking force and 41.3% for calcium retention. Assuming that the increased absorption of calcium (measured by a more sensitive dual isotope method) with SCF is retained, data from this study suggest that treatment with SCF would lead to additional calcium retention of 70 mg/d. Over a year this would account for an additional 25 g of calcium or 2.8% of total body calcium assuming that an adult skeleton has 900 g of calcium.

In conclusion, consumption of 12 g/d SCF positively influenced calcium absorption in adolescent girls and boys. SCF-induced absorption occurred after 24 hours which may be indicative of lower gut involvement. Significant increases were seen in proportions of members of the Bacteroidetes and Bifidobacteria, fermenters of resistant starches.

Example 3

Subjects and Methods
Methods

Gut microbiota composition in representative samples with (10 g/day dose ("D10") and 20 g/day dose ("D20")) and without (0 g/day dose ("D0")) SCF dietary treatment were determined using Illumina MiSeq high throughput sequencing instead of 454 pyrosequencing. The data is used to determine proportional increases or decreases in populations that are associated with differences in diet supplementation. There are five steps for gut microbial community analysis that were performed: (1) Fecal samples collected at the beginning and end of each randomly assigned diet SCF supplementation were homogenized in preparation for DNA extractions (a total of six samples per subject with the exception of subject 103 who did not submit a D0 beginning fecal sample); (2) Total fecal DNA was extracted using the Fast DNA™ Soil Spin kit and FastPrep™ system; (3) The extracted DNA was subjected to PCR using primers that target the Bacteria 16S rRNA gene; (4) The PCR products were sequenced using the Illumina MiSeq; (5) Sequences were analyzed using the QIIME pipeline to determine quantitative changes in microbial community members resulting from soluble corn fiber treatment.

Fecal Processing and DNA Extraction

Frozen fecal samples were processed and the DNA was extracted as provided in Example 2.

Microbial Community Composition

The phylogenetic diversity of bacterial communities was determined using 16S rRNA gene sequences obtained from high throughput paired end MiSeq technology (Illumina), and primers that amplify the V3-V4 region of the 16S rRNA gene were used. Multiple samples were run and differentiated using a combination of 8-bp tagged forward primer and 8-bp tagged reverse primers using a step out protocol that uses two PCR runs. The first PCR specifically amplifies the 16S rRNA gene from fecal samples extracts. Unincorporated primers and nucleotides were separated from PCR amplicons using Agencourt AMPure XP kit (Becker). The second PCR was used to add bitags to the amplicons (from the first run) that are needed for Illumina sequencing and purified again using the Agencourt AMPure XP kit. All PCR was performed using Q5® High Fidelity DNA Polymerase (New England Biolabs) to minimize error rate during polymerization. Purified amplicons were quantified by fluorometry after staining using the PicoGreen DNA Assay Kit. Amplicons from each sample were combined in equivalent quantities sequenced using the MiSeq instrument (Illumina)

Sequence Analysis

Sequences were pre-processed to remove primer tags and low quality sequences, and then analyzed using the QIIME pipeline. MiSeq Illumina sequences of 16S rRNA gene fragments were analyzed using both OTU-based and taxonomy based on phylogenetic trees. OTU was defined as a group based strictly on sequence similarity and not aligned to a known taxonomy. Sequences were first prefiltered and OTU assignments made using the uclust method and the Greengenes core sequences using a 60% threshold value (as recommended by QIIME developers). Representative OTU sequences were obtained after sequence alignment using PyNast to filter out sequences that did not align with the Greengenes core sequences. Taxonomic assignments were made using the RDP classifier at 80% confidence and the Greengenes database. Rarefaction analysis was used to obtain an estimation of sequence coverage of the community. Alpha biodiversity estimations were calculated to compare microbiota diversity within subjects under specific SCF treatments. Beta diversity comparisons between communities were made using "Fast UniFrac" analysis of phylogenetic distances as well as non-phylogenetic distance analysis using Euclidean distances. All alpha and beta diversity measures were made using equivalent number of taxa (based lowest number of sequences obtained from a single sample) that were randomly chosen using multiple rarefaction results (10 iterations).

Statistical Analyses

Friedman analysis (non-parametric equivalent to ANOVA) was used for an overall comparison of average proportions of genera in subjects at beginning (B) and end (E) of each SCF treatment. The Wilcoxon signed ranks test was then used to determine significant differences pairwise comparisons of samples from the beginning and end of each treatment phase as well as between end samples. Student's T-test was used to determine significant differences between alpha diversity measures. Significant differences in beta diversity between communities were determined using per-MANOVA a non-parametric multivariate statistical tool available in the Paleontological Statistics package version 2.16 (PAST software, http://folk.uio.no/ohammer/past/index.html). Bonferroni correction was applied to all statistical tests.

Results

The number of fecal samples analyzed for the 28 individuals was 167, six per individual with the exception of one subject who did not provide a beginning sample for the 0 g-diet supplementation experiment (Table 7). For this reason the statistical results presented in this report are based on data from only 27 subjects. The subjects were administered 10 g/day of SCF (D10), 20 g/day of SCF (D20), and no SCF (D0).

Number of Sequences

A total of 12,979,388 high quality merged sequences were obtained using MiSeq Illumina sequencing with an average of 77,720.9 sequences (±28,401) per sample, and ranged from 28,854 to 262,312 sequences per sample (Table 7). The lowest number of sequences obtained was 28,854 therefore all subsequent analyses were rarefied to 28,800 sequences per sample. To obtain a rarefied dataset, 10 iterations of randomly choosing 28,800 sequences from each dataset was performed then datasets were merge to obtain a set of 28,8000 sequences that were representative of each sample.

TABLE 7

Subjects included in the microbial community analysis and number of sequences from each fecal sample collected.

| Subject ID | B-D10* | E-D10 | B-D20 | E-D20 | B-D0 | E-D0 | Mean |
|---|---|---|---|---|---|---|---|
| 101 | 35648 | 95561 | 28854 | 81110 | 39956 | 127868 | 68166 |
| 102 | 32756 | 88022 | 53025 | 79399 | 39773 | 102533 | 65918 |
| 103** | 46731 | 83639 | 62571 | 57150 | ND | 114458 | 72910 |
| 105 | 71802 | 87419 | 77341 | 97803 | 78244 | 135063 | 91279 |
| 106 | 47326 | 78151 | 33267 | 92006 | 43006 | 98303 | 65343 |
| 107 | 41246 | 84315 | 34342 | 77309 | 37403 | 107778 | 63732 |
| 108 | 69813 | 71916 | 104705 | 58411 | 76103 | 70721 | 75278 |
| 109 | 48771 | 90250 | 32212 | 59657 | 39759 | 64715 | 55894 |
| 110 | 104086 | 80540 | 70670 | 87591 | 81174 | 102184 | 87708 |

TABLE 7-continued

Subjects included in the microbial community analysis and number of sequences from each fecal sample collected.

| Subject ID | B-D10* | E-D10 | B-D20 | E-D20 | B-D0 | E-D0 | Mean |
|---|---|---|---|---|---|---|---|
| 111 | 40890 | 74227 | 39385 | 86600 | 39783 | 84159 | 60841 |
| 112 | 37436 | 83953 | 38347 | 65681 | 42727 | 79281 | 57904 |
| 113 | 44561 | 73287 | 41348 | 67915 | 30805 | 53853 | 51962 |
| 114 | 82124 | 100597 | 70023 | 99104 | 67147 | 93323 | 85386 |
| 115 | 42685 | 85418 | 48484 | 85940 | 54404 | 93652 | 68431 |
| 116 | 55328 | 104198 | 62443 | 99053 | 38824 | 99359 | 76534 |
| 117 | 45551 | 70450 | 66727 | 119448 | 40043 | 78325 | 70091 |
| 118 | 70595 | 86264 | 85866 | 96618 | 83459 | 98271 | 86846 |
| 119 | 46358 | 80466 | 47594 | 106314 | 46887 | 98310 | 70988 |
| 120 | 57301 | 96805 | 66532 | 101655 | 52993 | 124090 | 83229 |
| 121 | 53277 | 72966 | 53345 | 76849 | 66119 | 137385 | 76657 |
| 122 | 76244 | 105777 | 88763 | 119395 | 71736 | 81078 | 90499 |
| 124 | 86440 | 112472 | 73716 | 94871 | 112156 | 79607 | 93210 |
| 125 | 92836 | 90916 | 83968 | 81214 | 69313 | 98037 | 86047 |
| 126 | 101758 | 127714 | 87905 | 89984 | 110822 | 101913 | 103349 |
| 127 | 108740 | 88143 | 85892 | 94263 | 103970 | 59492 | 90083 |
| 128 | 93626 | 95191 | 56287 | 77558 | 68134 | 89239 | 80006 |
| 129 | 81034 | 93014 | 81428 | 75555 | 56459 | 48613 | 72684 |
| 130 | 262312 | 66058 | 87767 | 116323 | 95907 | 118085 | 124409 |

*B- denotes the beginning sample, and E- denotes the end sample.
**excluded from statistical analyses because of missing sample Comparison of Phyla Represented in Sequence Data There were 13 phyla, *Actinobacteria, Bacteroidetes, Firmicutes, Proteobacteria, Chloroflexi, Cyanobacteria, Fusobacteria, Lentisphaerae, Synergistetes*, TM7, Tenericutes, [Thermi] and Verrucomicrobia found in the microbial communities of the 28 subjects. In addition, the primers amplified some sequences from the domain *Archaea* and other Bacteria that currently cannot be classified. But more than 99% of the sequences were from four phyla, *Actinobacteria, Bacteroidetes, Firmicutes* and *Proteobacteria*. Across all samples from all subjects the Firmicutes was the dominant phylum with an average of 65.8% followed by Bacteroidetes (26.0%), Actinobacteria (6.2%) and *Proteobacteria* (1.8%) (FIG. 1). There was no significant difference in proportions of phyla between the beginning and end samples from any of the SCF test treatments. There were also no significant differences found at the Class and Order level of taxonomic classification. *Archaea* are an important group that should be monitored in the future but because the primers used in this study were not developed for their inclusion we do not think it is proper to use their presence (or absence) in our assessment.

Comparison of Families Represented in Sequence Data

ANOVA of the taxa at the family level indicated there was a significant difference only within the phylum Bacteroidetes. The Bacteroidetes included the families Bacteroidaceae, Porphyromonadaceae, Prevotellaceae, and Rikenellaceae and tentative new families [Barnesiellaceae], [Odoribacteraceae], [Paraprevotellaceae], [Weeksellaceae], RF16, S24-7, and three other families. Families listed as [tentative] and "other" are those have yet to be officially classified, mainly because these groups are recent discoveries based on molecular analyses of which some have no representatives in culture to use for taxonomic assignment. ANOVA indicated that there were significant differences in the Porphyromonadaceae that was supported by Bonferroni correction (p<0.0001).

Comparison of Genera Represented in Sequence Data

For further resolution the same comparisons were made at the genus level of phylogenetic classification using non-parametric statistics. Of the 235 genera (or genera equivalents) identified in analysis of all subject samples that were sequenced, a subset of only 24 genera comprised >1% of the community in at least one of the samples and represented about 90% of the communities (results not shown). Although some genera made up a small proportion of the communities they did differ significantly. Genera that differed significantly were *Parabacteroides, Bacteroides, Dorea, Lachnospira*, an unclassified *Ruminococcus*, unclassified Lachnospiraceae and "other" Bacteria (Table 8) based on Friedman analysis (non-parametric equivalent to ANOVA) with Bonferonni correction.

TABLE 8

Friedman analysis (non-parametric equivalent to ANOVA) of average proportions of genera* in subjects at beginning (B) and end (E) of each SCF treatment (10, 20, and 0 g/day)

|  | B-D10 (%) | E-D10 (%) | B-D20 (%) | E-D20 (%) | B-D0 (%) | E-D0 (%) | P | Bonferroni Corrected P |
|---|---|---|---|---|---|---|---|---|
| *Parabacteroides* | 0.90 | 2.11 | 1.12 | 3.01 | 0.99 | 1.06 | 0.0000 | 0.0000 |
| Uncl. Lachnospiraceae | 6.35 | 11.39 | 6.04 | 13.08 | 5.87 | 6.32 | 0.0000 | 0.0000 |
| Reclassified [*Ruminococcus*] | 3.75 | 2.38 | 2.48 | 1.89 | 3.58 | 3.74 | 0.0000 | 0.0000 |
| *Dorea* | 1.08 | 1.04 | 1.22 | 0.70 | 1.14 | 1.26 | 0.0000 | 0.0015 |
| Other Bacteria | 0.07 | 0.05 | 0.12 | 0.06 | 0.11 | 0.04 | 0.0000 | 0.0016 |
| *Lachnospira* | 1.14 | 0.67 | 1.43 | 0.66 | 1.26 | 0.94 | 0.0000 | 0.0067 |
| *Bacteroides* | 14.75 | 11.09 | 16.18 | 9.62 | 15.64 | 13.74 | 0.0001 | 0.0216 |

TABLE 8-continued

Friedman analysis (non-parametric equivalent to ANOVA) of average proportions of genera*
in subjects at beginning (B) and end (E) of each SCF treatment (10, 20, and 0 g/day)

|  | B-D10 (%) | E-D10 (%) | B-D20 (%) | E-D20 (%) | B-D0 (%) | E-D0 (%) | P | Bonferroni Corrected P |
|---|---|---|---|---|---|---|---|---|
| *Turicibacter* | 0.22 | 0.12 | 0.12 | 0.13 | 0.15 | 0.27 | 0.0011 | 0.2545 |
| *Dialister* | 0.64 | 0.86 | 0.74 | 1.17 | 0.55 | 0.46 | 0.0016 | 0.3796 |
| SMB53 | 2.46 | 1.92 | 1.89 | 1.38 | 2.08 | 1.93 | 0.0026 | 0.6035 |
| *Ruminococcus* | 5.12 | 7.15 | 5.89 | 7.70 | 5.00 | 5.94 | 0.0041 | 0.9555 |
| *Streptococcus* | 0.39 | 0.18 | 0.19 | 0.46 | 0.37 | 0.22 | 0.0048 | 1 |
| *Adlercreutzia* | 0.06 | 0.05 | 0.06 | 0.04 | 0.06 | 0.06 | 0.0057 | 1 |
| *Butyricimonas* | 0.13 | 0.10 | 0.17 | 0.16 | 0.17 | 0.18 | 0.0089 | 1 |
| *Porphyromonas* | 0.00 | 0.01 | 0.00 | 0.00 | 0.00 | 0.01 | 0.0094 | 1 |
| Other Clostridiaceae | 0.32 | 0.09 | 0.30 | 0.11 | 0.25 | 0.26 | 0.0151 | 1 |
| *Fusobacterium* | 0.000 | 0.001 | 0.001 | 0.000 | 0.000 | 0.001 | 0.0156 | 1 |
| Uncl Alcaligenaceae | 0.001 | 0.002 | 0.001 | 0.002 | 0.001 | 0.001 | 0.0162 | 1 |
| *Prevotella* | 5.73 | 6.35 | 6.30 | 4.72 | 6.70 | 6.64 | 0.0168 | 1 |
| *Varibaculum* | 0.000 | 0.001 | 0.002 | 0.001 | 0.000 | 0.001 | 0.0170 | 1 |
| Uncl. Erysipelotrichaceae | 0.01 | 0.01 | 0.01 | 0.00 | 0.01 | 0.01 | 0.0231 | 1 |
| *Akkermansia* | 0.000 | 0.003 | 0.001 | 0.001 | 0.001 | 0.001 | 0.0232 | 1 |
| *Campylobacter* | 0.001 | 0.001 | 0.002 | 0.001 | 0.000 | 0.001 | 0.0233 | 1 |
| *Granulicatella* | 0.003 | 0.001 | 0.001 | 0.001 | 0.003 | 0.002 | 0.0241 | 1 |
| *Sutterella* | 0.80 | 0.79 | 1.01 | 0.93 | 1.10 | 1.06 | 0.0245 | 1 |
| Uncl. Enterobacteriaceae | 0.22 | 0.36 | 0.26 | 0.15 | 0.24 | 0.47 | 0.0255 | 1 |
| *Corynebacterium* | 0.00 | 0.00 | 0.00 | 0.01 | 0.06 | 0.00 | 0.0297 | 1 |
| *Acidaminococcus* | 0.10 | 0.12 | 0.05 | 0.15 | 0.07 | 0.10 | 0.0301 | 1 |
| *Odoribacter* | 0.39 | 0.29 | 0.45 | 0.88 | 0.36 | 0.50 | 0.0304 | 1 |
| WAL_1855D | 0.00 | 0.00 | 0.00 | 0.00 | 0.00 | 0.00 | 0.0312 | 1 |
| *Anaerostipes* | 0.22 | 0.14 | 0.18 | 0.13 | 0.33 | 0.22 | 0.0344 | 1 |
| *Abiotrophia* | 0.00 | 0.00 | 0.00 | 0.00 | 0.00 | 0.00 | 0.0423 | 1 |

*Only genera that differed significantly (p < 0.05) are included in the table
"Uncl (Unclassified)" designation indicates that the sequence likely belongs to a new genus that has yet to be described but there is sufficient information that supports the identification of a new genus.
"Other" designation also for unclassified taxa but at higher taxonomic levels, i.e., class, order or family.

Pairwise comparison (Wilcoxon Signed Rank test with Bonferroni correction) of proportional averages of all genera in the beginning and end samples collected within SCF treatments were made to identify the treatments in which these taxa differed significantly. Proportions of *Parabacteroides* and an unclassified Lachnospiraceae (Table 8) were significantly greater at the ends of diets D10 and D20 compared to the beginning. In addition, at the end of diet D10 there was a significant increase in *Akkermansia* and decrease in reclassified [*Ruminococcus*]. At the end of diet D20 there were significant decreases in *Bacteroides* and *Lachnospira*. At the end of diet D0 there was a significant decrease in "other" Bacteria but this is not a single taxonomic group. Therefore, unlike the other two diet treatments there were no significant differences in taxa in subjects after consuming diet D0.

TABLE 8

Comparison of average proportions (%) of genera in subjects that significantly
differed (Wilcoxon signed rank test after Bonferroni correction, p < 0.05)
between the beginning (B) and end (E) of each SCF treatment (10, 20, and 0 g/day)

| Phylum/Genus | B-D10 | E-D10 | p | B-D20 | E-D20 | p | B-D0 | E-D0 | p |
|---|---|---|---|---|---|---|---|---|---|
| Bacteroidetes | | | | | | | | | |
| *Bacteroides* | 14.7 | 11.1 | ns | 16.2 | 9.6 | 0.011 | 15.6 | 13.7 | ns |
| *Parabacteroides* | 0.9 | 2.1 | 0.002 | 1.1 | 3.0 | 0.001 | 1.0 | 1.1 | ns |
| Firmicutes | | | | | | | | | |
| *Lachnospira* | 1.1 | 0.7 | ns | 1.4 | 0.7 | 0.002 | 1.3 | 0.9 | ns |
| Unclassified Lachnospiraceae | 6.4 | 11.4 | 0.001 | 6.0 | 13.1 | 0.0003 | 5.9 | 6.3 | ns |
| reclassified *Ruminococcus* | 3.7 | 2.4 | 0.011 | 2.5 | 1.9 | ns | 3.6 | 3.7 | ns |
| Verrucomicrobia | | | | | | | | | |
| *Akkermansia* | 0.000 | 0.003 | 0.020 | 0.001 | 0.001 | ns | 0.001 | 0.001 | ns |
| Other Bacteria | 0.07 | 0.05 | ns | 0.12 | 0.06 | ns | 0.11 | 0.04 | 0.001 |

Furthermore, pairwise comparisons of diets D10, D20, and D0 end samples substantiated the differences in communities (Table 9). There was a potential dosage effect on the *Parabacteroides*, this was indicated by significantly greater proportions after diet D20 compared to D10 that was greater than after diet D0. The same trend was found for the unclassified Lachnospiraceae and *Dialister*, which were significantly greater at the end of diets D10 and D20 compared to D0 but diets D10 and D20 were not significantly different. Also, there was a significantly greater proportion of *Bifidobacterium* at the end of diet D20 compared to D0. At the end of diets D10 and/or D20 compared to D0 there were significantly lower proportions of *Anaerostipes*, *Dorea*, reclassified [*Ruminococcus*], and unclassified Erysipelotrichaceae. At the beginning of SCF diet treatment there were also significant differences in proportions of reclassified [*Ruminococcus*], Enterococcus and *Campylobacter*. The significantly greater proportion of reclassified [*Ruminococcus*] at the beginning of diet D20 potentially factored into finding a significant difference in this taxon in the comparison of the beginning and end samples.

TABLE 9a

Comparison of average proportions of genera* that differed significantly at the beginning (B) of each SCF treatment (10, 20, and 0 g/day) using Bonferroni corrected Wilcoxon Sum Rank Test (non-parametric)

| Phylum | Genus | B-D10 (%) | B-D20 (%) | B-D0 (%) |
|---|---|---|---|---|
| Firmicutes | Reclassified *Ruminococcus* | 3.75 | 2.48 | 3.58 |
| Firmicutes | *Enterococcus* | 0.001 | 0.027 | 0.009 |
| Proteobacteria | *Campylobacter* | 0.001 | 0.002 | 0.000 |

TABLE 9b

Comparison of average proportions of genera* in subjects at end (E) of each SCF treatment (10, 20, and 0 g/day) using Bonferroni corrected Wilcoxon Sum Rank Test (non-parametric)

| Phylum | Genus | E-D10 (%) | E-D20 (%) | E-D0 (%) |
|---|---|---|---|---|
| Actinobacteria | *Bifidobacterium* | 4.23 | 5.06 | 3.24 |
| Bacteroidetes | *Parabacteroides* | 2.11 | 3.01 | 1.06 |
| Firmicutes | *Anaerostipes* | 0.13 | 0.13 | 0.22 |
| Firmicutes | *Dorea* | 1.04 | 0.70 | 1.26 |
| Firmicutes | Reclassified *Ruminococcus* | 2.38 | 1.89 | 3.74 |
| Firmicutes | Unclassified Lachnospiraceae | 11.39 | 13.08 | 6.32 |
| Firmicutes | *Dialister* | 0.86 | 1.17 | 0.46 |
| Firmicutes | Unclassified Erysipelotrichaceae | 0.006 | 0.004 | 0.008 |

Without being bound to a particular theory, the increase in proportion of *Parabacteroides*, unclassified Lachnospiraceae and *Dialister* after diets D10 and D20 suggests that these microbes are involved in SCF fermentation.

Comparison of Alpha Diversity

Figure 5:
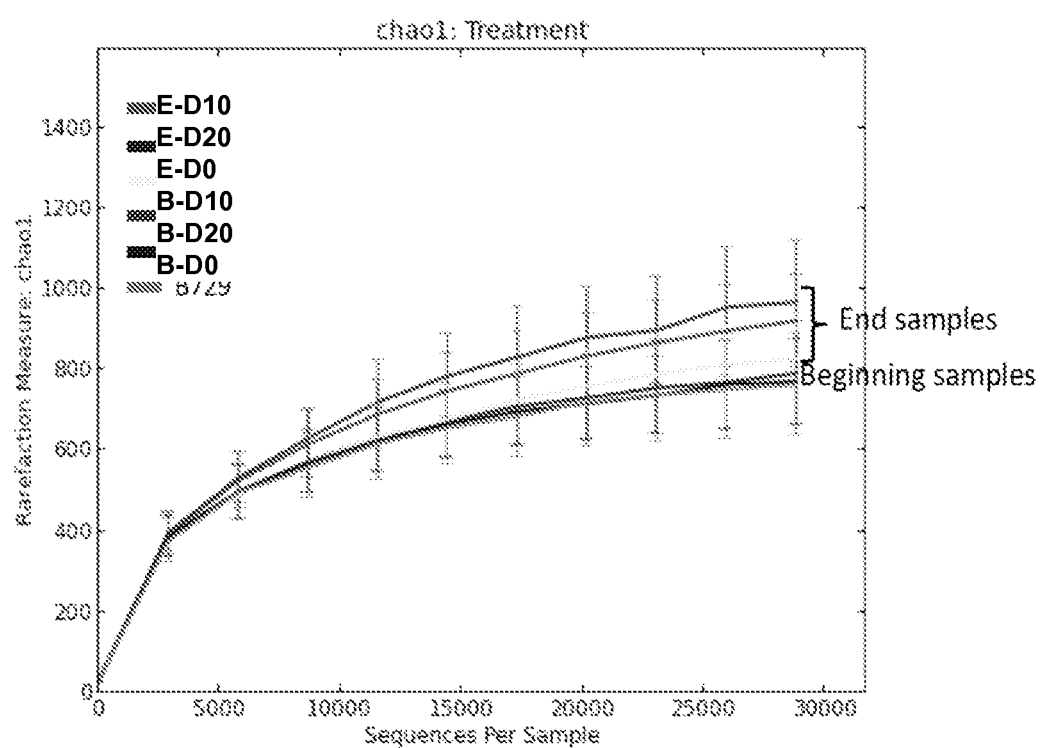
FIG. 5 shows the rarefaction analysis of Chao1 diversity measures made from beginning (B) and end (E) fecal samples collected from subjects on different SCF diet treatment.

There were significant differences ($p<0.05$) in alpha diversity measures between the beginning and end communities under each SCF diet (Table 10). The alpha diversity provides a metric for diversity within a treatment. Using the Chao1 measure these differences were found for both SCF diets D10 and D20 and not D0 (Table 10, FIG. 5). Whereas using Observed Species the difference was only significant for diet D20. No significant differences were found for PD Whole Tree (Table 10a). Whereas pairwise comparison of the diversity in the end samples indicated there were significant differences between all Chao1 values and between end of D10 and D20 versus D0. The differences in significance among the diversity indices tested are because the algorithms for each of these alpha diversity measures are quite different with emphasis on different criteria. For example PD whole tree is a phylogenetic measures whereas the other two are not. Chao1 is a measure of species richness and observed species sums up the number of unique OTUs. Without being bound to a particular theory, it is believed that the SCF diet was increasing the number of taxa in the samples.

TABLE 10a

Comparison of mean ± standard deviation of Alpha diversity values. Significant differences between beginning and end within each treatment

| | B-D10 | E-D10 | B-D20 | E-D20 | B-D0 | E-D0 |
|---|---|---|---|---|---|---|
| Chao 1 | 1141 ± 155 | 1282 ± 192 | 1146 ± 154 | 1402 ± 276 | 1152 ± 186 | 1104 ± 126 |
| PD whole tree | 30.8 ± 4.2 | 31.2 ± 4.2 | 31.2 ± 4.1 | 31.7 ± 3.7 | 30.8 ± 4.2 | 29.8 ± 4.4 |
| Observed Species | 624.8 ± 82.3 | 634.5 ± 83.8 | 619.6 ± 91.4 | 649.6 ± 75.5 | 615.1 ± 83.4 | 601.4 ± 83.5 |

TABLE 10b

Significant differences between beginning and end samples within each treatment

|  | B-D10 | E-D10 | B-D20 | E-D20 | B-D0 | E-D0 |
|---|---|---|---|---|---|---|
| Chao 1 | 1141 ± 155 | 1146 ± 154 | 1152 ± 186 | 1282 ± 192 | 1402 ± 276 | 1104 ± 126[e] |
| PD whole tree | 30.8 ± 4.2 | 31.2 ± 4.1 | 30.8 ± 4.2 | 31.2 ± 4.2 | 31.7 ± 3.7 | 29.8 ± 4.4 |
| Observed Species | 624.8 ± 82.3 | 619.6 ± 91.4 | 615.1 ± 83.4 | 634.5 ± 83.8 | 649.6 ± 75.5 | 601.4 ± 83.5 |

Community Comparisons Using Beta Diversity

Figure 6:
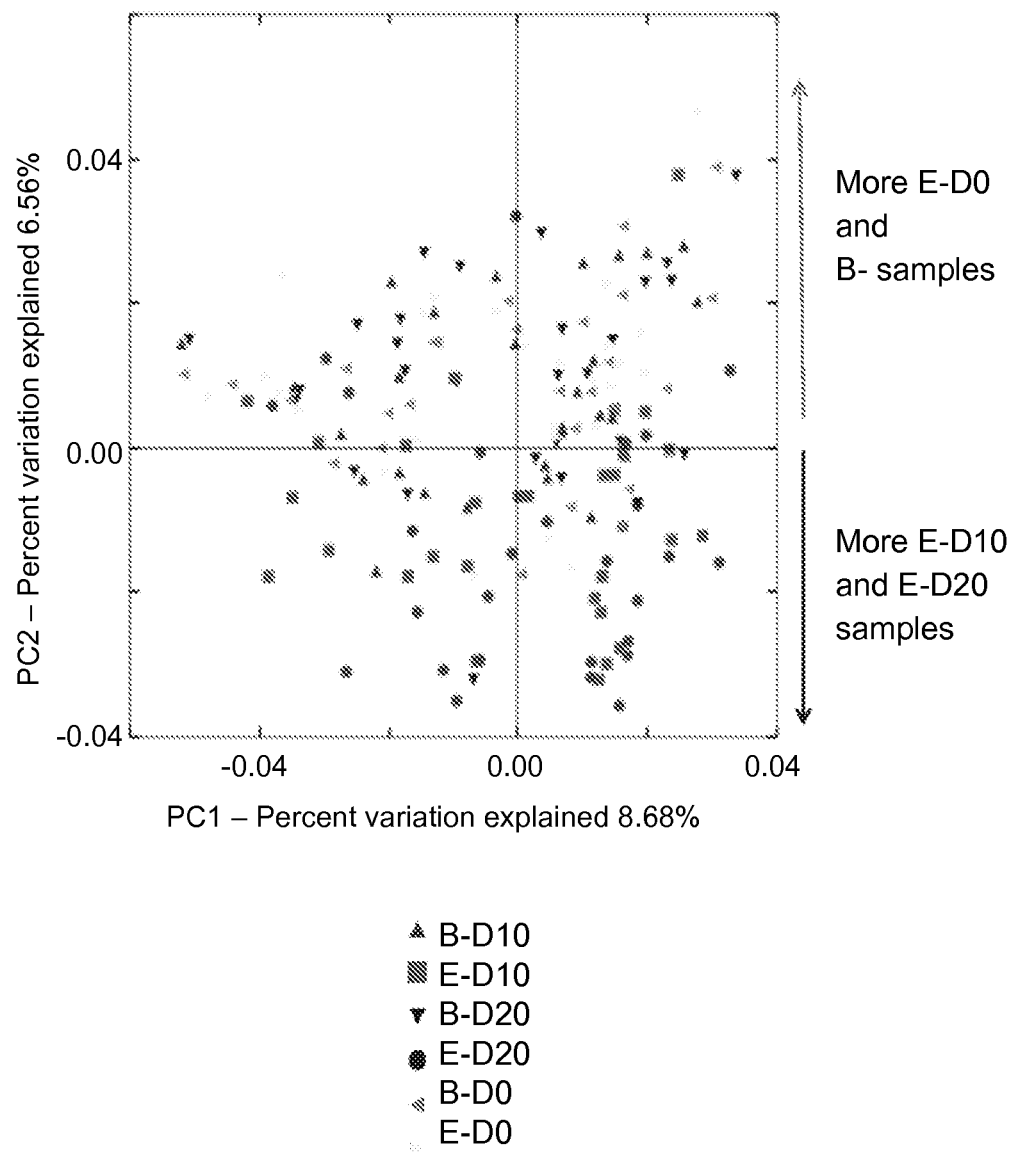
FIG. 6 shows Principal Coordinate Analysis (PCoA) of Jackknife Bray Curtis distances (normalized Manhattan distance) of community composition coded SCF diet supplement samples collected at the beginning (B) and end (E) of the SCF treatment.
Figure 7:
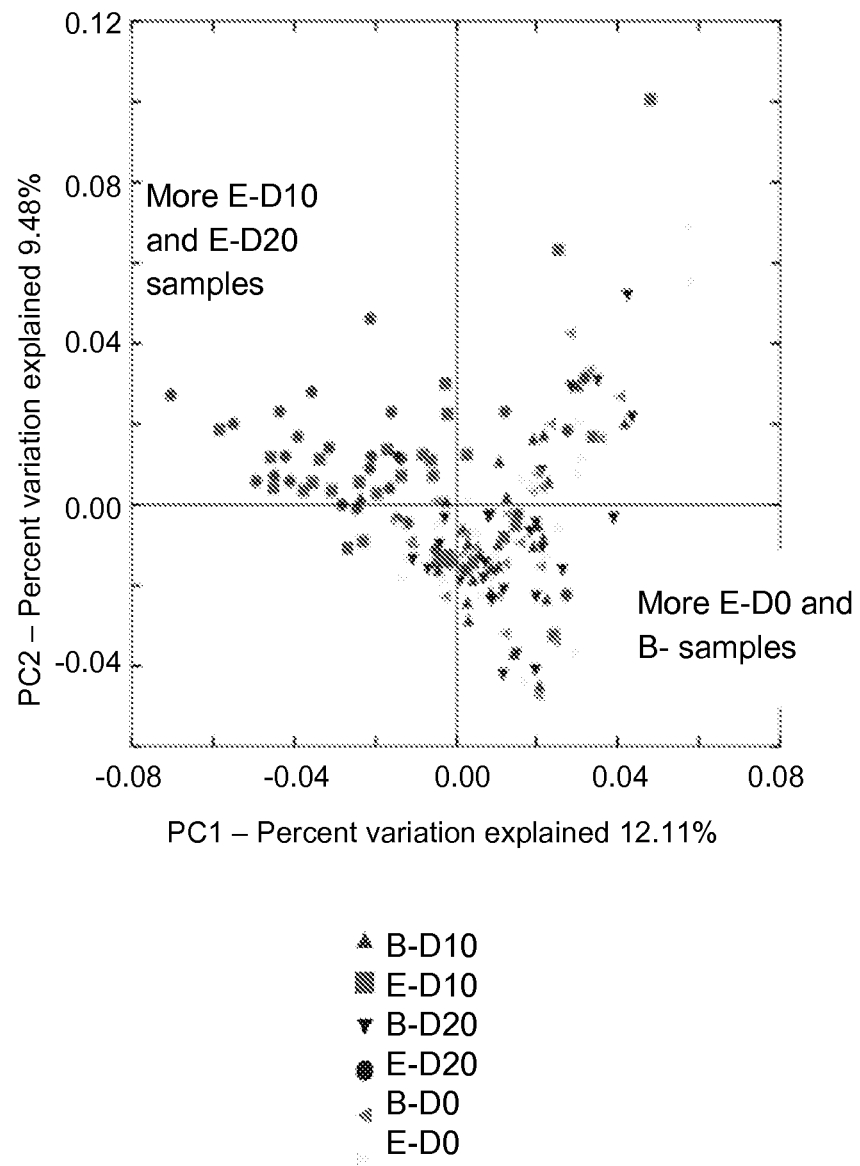
FIG. 7 shows Principal Coordinate Analysis (PCoA) of Jackknife Bray Euclidean distances of community composition coded SCF diet supplement samples collected at the beginning (B) and end (E) of the SCF treatment.
Figure 8:
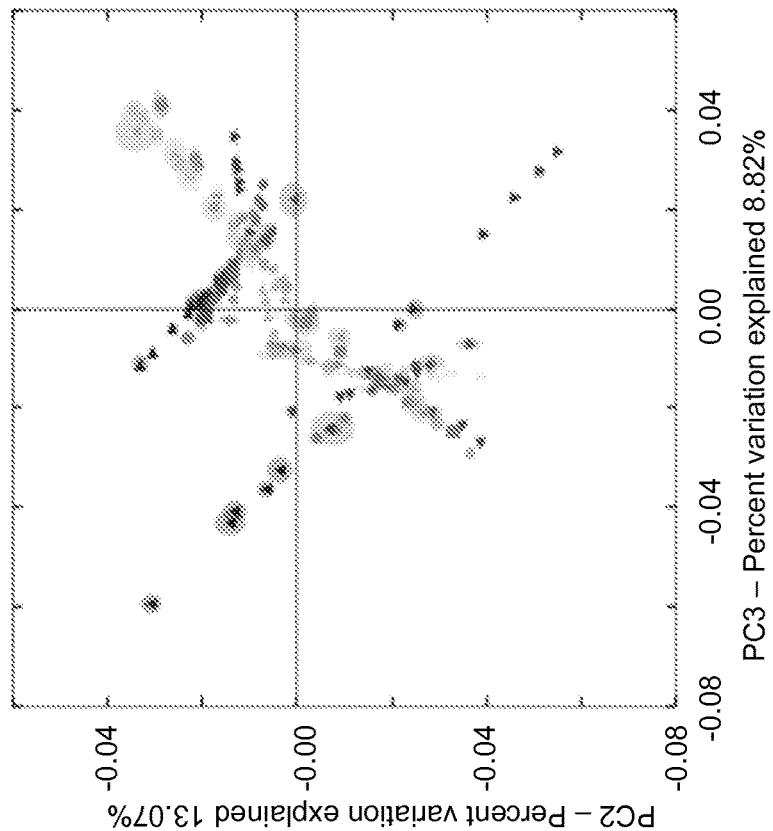
FIG. 8 shows Principal Coordinate Analysis (PCoA) of Jackknife Analysis of Unifrac G phylogenetic distances of community composition collected from subjects at the beginning (B) and end (E) of the SCF treatment.
Figure 8:
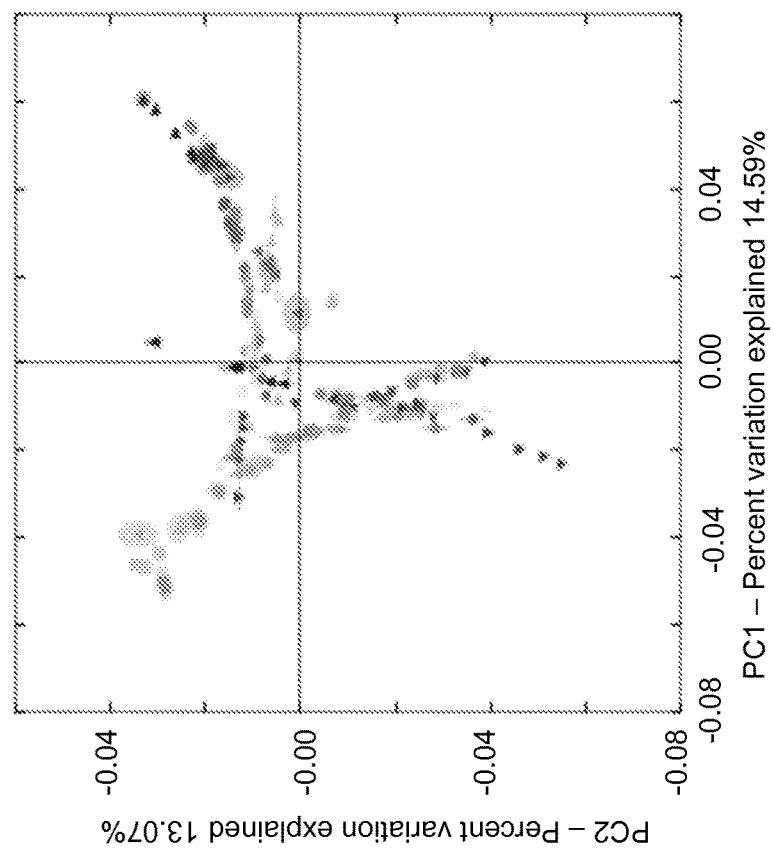

Comparisons between communities (beta diversity) revealed separation of some communities dependent on the distance measures used. Non-phylogenetic Euclidean distances (Binary Euclidean and Bray Curtis) and phylogenetic distances (Unifrac G, Unifrac weighted, and Unifrac unweighted) with jackknife were tested to determine differences in community structure between samples and factors likely contributing to these differences. Principal Coordinate Analysis (PCoA) clustering of non-phylogenetic Euclidean distances indicated communities at the end of SCF treatments D10 and D20 separated from those at the end of the D0 and all the beginning samples (FIGS. 6 and 7). Separation was most evident using binary Euclidean distances (FIG. 7). Separation can be seen across the first PCoA axis that accounted for 12.11% of variation and to some extent along the second PCoA axis that accounts for 9.48% of variation. Whereas using any of the Unifrac phylogenetic distances clustering of samples were more by subject rather than by treatment (example Unifrac G, FIG. 8). This indicates that the phylogenetic composition of communities is more similar within a subject than between subjects. This is similar to previous reports of high variation between the gut microbiome of humans. These Euclidean and phylogenetic distances are calculated using different criteria that provide insight into factors contributing to differences in gut microbial communities. For example, Euclidean distances are based on presence or absence of every OTU (operational taxonomic unit) in each community. This indicates that the presence or absence of specific taxa is contributing to the differences in the community.

Non-Parametric Permutation Multivariate ANOVA

Non-parametric permutation multivariate ANOVA (perMANOVA) after Bonferroni correction revealed significant differences between treatments that were seen as clusters in the Principal Coordinate (PCoA) scatterplots of beta diversity analysis. Significant differences were found between communities in samples from the beginning and end samples of diets D10 and D20 with their respective beginning samples using the Euclidean distances measured (Bray Curtis, binary Euclidean) but not the phylogenetic measures (Unifrac distances) (Table 11, results also shown in FIGS. 6-8). There were also significant differences in the Euclidean and Bray Curtis distances between the end samples of diet D20 compared to the end D0. End samples of diets D10 and D0 also differed significantly but only using Euclidean distances. There were also differences in the Unifrac G distances but because differences were also found between beginning samples it may not be a result of the SCF treatments. Prior to Bonferroni corrections there were more significant differences (Table 11) but here we have chosen to focus on the more stringent cutoff. However, the data has been included in the report because the stringency of Bonferroni can include false negatives. Regardless, these results clearly illustrates that the microbial communities of the subjects at the end of SCF diet treatment D20 differed the most, suggesting that it was the code for the highest SCF dose given to the subjects.

TABLE 11

Summary of per MANOVA using various beta distance measures of communities (average proportion of genera) between the beginning (B) and end (E) of each SCF treatment (10, 20, and 0 g/day)

| Distance Measure | B-D10 v E-D10 | B-D20 v E-D20 | B-D0 v E-D0 | B-D10 v B-D20 | B-D10 v B-D0 | B-D20 v B-D0 | E-D10 v E-D20 | E-D10 v E-D0 | E-D20 v E-D0 |
|---|---|---|---|---|---|---|---|---|---|
| Bray-Curtis | 0.0003 | 0.0000 | 1.0000 | 0.9999 | 1.0000 | 0.9999 | 0.9994 | 0.0038 | 0.0000 |
| Euclidean | 0.0000 | 0.0000 | 0.9999 | 0.9998 | 1.0000 | 0.9985 | 0.9778 | 0.0004 | 0.0000 |
| Unifrac g | 0.3002 | 0.2936 | 0.0056 | 0.0106 | 0.0115 | 0.0020 | 0.0311 | 0.0000 | 0.0000 |
| Unifrac unweighted | 0.4507 | 0.0360 | 0.8434 | 1.0000 | 1.0000 | 0.9984 | 0.9999 | 0.9538 | 0.3064 |
| Unifrac weighted | 0.3544 | 0.0133 | 0.9876 | 0.9030 | 0.9863 | 0.9878 | 0.8203 | 0.3676 | 0.0468 |
| With Bonferroni correction | | | | | | | | | |
| Bray-Curtis | 0.0051 | 0.0002 | 1.0000 | 1.0000 | 1.0000 | 1.0000 | 1.0000 | 0.0575 | 0.0003 |
| Euclidean | 0.0003 | 0.0002 | 1.0000 | 1.0000 | 1.0000 | 1.0000 | 1.0000 | 0.0054 | 0.0002 |
| Unifrac g | 1.0000 | 1.0000 | 0.0846 | 0.1590 | 0.1727 | 0.0303 | 0.4670 | 0.0003 | 0.0002 |
| Unifrac unweighted | 1.0000 | 0.5400 | 1.0000 | 1.0000 | 1.0000 | 1.0000 | 1.0000 | 1.0000 | 1.0000 |
| Unifrac weighted | 1.0000 | 0.1992 | 1.0000 | 1.0000 | 1.0000 | 1.0000 | 1.0000 | 1.0000 | 0.7026 |

The foregoing description of embodiments of the present invention has been presented for the purposes of illustration and description. It is not intended to be exhaustive or to limit the invention to the precise forms disclosed. As the person of skill in the art will recognize, many modifications and variations are possible in light of the above teaching. It will be apparent to those skilled in the art that various modifications and variations can be made to the present invention without departing from the scope of the invention. Thus, it is intended that the present invention cover the modifications and variations of this invention provided they come within the scope of the claims and their equivalents.

We claim:

1. An edible composition for increasing one or more colonic bacteria populations in a subject, the edible composition comprising soluble corn fiber and one or more bacterial populations, wherein at least one of the one or more bacteria populations is of a genus selected from the group consisting of *Parabacteroides, Oscillibacter, Alisupes*, and *Anaerococcus*, wherein the soluble corn fiber is made by a process comprising:
   providing an aqueous feed composition that comprises a syrup made by hydrolysis of corn starch, the aqueous feed composition comprising linear dextrose oligomers, and that has a solids concentration of at least 90% by weight; and
   contacting the feed composition for a time in the range of 0.1-15 minutes at a temperature of at least 149° C. with at least one catalyst that accelerates the rate of cleavage or formation of glucosyl bonds for a time sufficient to cause formation of non-linear dextrose oligomers, wherein the at least one catalyst is an acid added to the feed composition in an amount sufficient to make the pH of the feed composition 1.0-2.5, wherein a product composition is formed in which the concentration of non-linear dextrose oligomers is at least twice as high as the concentration of linear dextrose oligomers, and in which the concentration of non-linear dextrose oligomers having a degree of polymerization of at least three is at least 50% by weight on a dry solids basis, the product composition being primarily digestion resistant, the product composition including less than 50% on a dry solids basis of residual monosaccharides,
   wherein the dextrose oligomers have a degree of polymerization of 2 to 30.

2. The edible composition of claim 1, further comprising one or more bacteria populations, each of a different genus selected from the group consisting of *Bacteroides* and *Dialister*.

3. The edible composition of claim 1, comprising one or more bacteria populations, each of a genus selected from the group consisting of *Parabacteroides*, and *Oscillibacter*.

4. The edible composition of claim 1, wherein at least one of the one or more bacteria populations is of a genus selected from the group consisting of *Parabacteroides, Alistipes*, and *Anaerococcus*.

5. The edible composition of claim 1, wherein at least one of the one or more bacterial populations is of the genus *Oscillibacter*.

6. The edible composition of claim 1, further comprising a bacterial population of the genus *Dialister*.

7. The edible composition of claim 1, wherein the composition comprises at least 2.5 g of soluble corn fiber per serving.

8. The edible composition of claim 1, wherein the composition further comprises calcium.

9. The edible composition according to claim 8, wherein the calcium is provided at an amount of at least about 50 mg mineral per dose or serving.

10. The edible composition of claim 1, wherein the composition is provided in a form selected from baked foods, breakfast cereal, dairy products, soy products, confections, jams and jellies, beverages (powdered and/or liquid), shakes, fillings, yogurts (dairy and non-dairy yogurts), kefirs, extruded and sheeted snacks, gelatin desserts, snack bars, meal replacement and energy bars, cheese and cheese sauces (dairy and non-dairy cheeses), edible and water-soluble films, soups, syrups, table top sweeteners, nutritional supplements, sauces, dressings, creamers, icings, ice cream, frostings, glazes, pet food, tortillas, meat and fish, dried fruit, infant and toddler food, and batters and breadings.

11. The edible composition of claim 1, wherein the food composition is in the form of an agglomerated powder, a nutritional supplement or a medicinal dosage form.

12. The edible composition of claim 1, further comprising a bacterial population of the genus *Bifidobacterium*.

13. The edible composition of claim 1, further comprising a bacterial population of the genus *Bacteroides* or the genus *Dialister*.

14. The method of claim 1, wherein at least one of the one or more bacterial populations is of the genus *Alistipes*, or *Anaerococcus*.

15. A method of increasing one or more colonic bacteria populations in a mammalian subject, each of a genus selected from the group consisting of *Parabacteroides, Oscillibacter, Alistipes*, and *Anaerococcus*, the method comprising administering to the subject an edible composition comprising soluble corn fiber and one or more bacterial populations, wherein at least one of the one or more bacteria populations is of a genus selected from the group consisting of *Parabacteroides, Oscillibacter, Alistipes*, and *Anaerococcus*, wherein the soluble corn fiber is made by a process comprising:
   providing an aqueous feed composition that comprises a syrup made by hydrolysis of corn starch, the aqueous feed composition comprising linear dextrose oligomers, and that has a solids concentration of at least 90% by weight; and
   contacting the feed composition for a time in the range of 0.1-15 minutes at a temperature of at least 149° C. with at least one catalyst that accelerates the rate of cleavage or formation of glucosyl bonds for a time sufficient to cause formation of non-linear dextrose oligomers, wherein the at least one catalyst is an acid added to the feed composition in an amount sufficient to make the pH of the feed composition 1.0-2.5, wherein a product composition is formed in which the concentration of non-linear dextrose oligomers is at least twice as high as the concentration of linear dextrose oligomers, and in which the concentration of non-linear dextrose oligomers having a degree of polymerization of at least three is at least 50% by weight on a dry solids basis, the product composition being primarily digestion resistant or primarily slowly digestible, the product composition including less than 50% on a dry solids basis of residual monosaccharides,
wherein the dextrose oligomers have a degree of polymerization of 2 to 30.

16. The method according to claim 15, wherein one or more of the colonic bacteria populations is increased by at least about 10% as compared to a non-treated subject.

17. The method according to claim 15, wherein the administration is performed such that fecal pH is reduced by at least about 1.5 pH units.

18. The method according to claim 15, wherein the increase in colonic bacteria population and/or the decrease in pH results in an increase in the bioavailability of calcium.

19. The method according to claim 15, wherein the method further increases calcium absorption by at least about 35% in the subject.

20. The method according to claim 15, wherein the soluble corn fiber is administered at a rate of at least about 2.5 g/day.

21. The method according to claim 15, wherein at least one of the one or more bacterial populations is of the genus *Oscillibacter*.

22. The method according to claim 15, wherein the administration is performed over the course of at least two weeks.

23. The method of claim 15, wherein at least one of the one or more bacterial populations is of the genus *Parabacteroides, Alistipes,* or *Anaerococcus*.

24. A method of increasing one or more colonic bacteria populations in a mammalian subject, each of a genus selected from the group consisting of *Parabacteroides, Oscillibacter, Alistipes,* and *Anaerococcus*, the method comprising administering to the subject an edible composition comprising soluble corn fiber and one or more bacterial populations, wherein at least one of the one or more bacteria populations is of a genus selected from the group consisting of *Parabacteroides, Oscillibacter, Alistipes,* and *Anaerococcus*, wherein the soluble corn fiber is made by a process comprising:

providing an aqueous feed composition that comprises a syrup made by hydrolysis of corn starch, the aqueous feed composition comprising linear dextrose oligomers, and that has a solids concentration of at least 90% by weight; and contacting the feed composition for a time in the range of 0.1-15 minutes at a temperature of at least 149° C. with at least one catalyst that accelerates the rate of cleavage or formation of glucosyl bonds for a time sufficient to cause formation of non-linear dextrose oligomers, wherein the at least one catalyst is an acid added to the feed composition in an amount sufficient to make the pH of the feed composition 1.0-2.5, wherein a product composition is formed in which the concentration of non-linear dextrose oligomers is at least twice as high as the concentration of linear dextrose oligomers, and in which the concentration of non-linear dextrose oligomers having a degree of polymerization of at least three is at least 50% by weight on a dry solids basis, the product composition being primarily digestion resistant or primarily slowly digestible, the product composition including less than 50% on a dry solids basis of residual monosaccharides, wherein the dextrose oligomers have a degree of polymerization of 2 to 30, wherein the administration is performed such that fecal pH is reduced by at least about 1.5 pH units, wherein the administration is performed such that the fecal pH is no more than about 5.5.

\* \* \* \* \*